US008420645B2

(12) United States Patent
Weng et al.

(10) Patent No.: US 8,420,645 B2
(45) Date of Patent: Apr. 16, 2013

(54) SALTS OF 2-FLUORO-N-METHYL-4-[7-(QUINOLIN-6-YL-METHYL)-IMIDAZO[1,2-B][1,2,4]TRIAZIN-2-YL]BENZAMIDE AND PROCESSES RELATED TO PREPARING THE SAME

(75) Inventors: Lingkai Weng, Malvern, PA (US); Lei Qiao, Downingtown, PA (US); Jiacheng Zhou, Newark, DE (US); Pingli Liu, Newark, DE (US); Yongchun Pan, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 746 days.

(21) Appl. No.: 12/469,360

(22) Filed: May 20, 2009

(65) Prior Publication Data

US 2009/0291956 A1      Nov. 26, 2009

Related U.S. Application Data

(60) Provisional application No. 61/054,995, filed on May 21, 2008.

(51) Int. Cl.
| *A01N 43/64* | (2006.01) |
| *A61K 31/53* | (2006.01) |
| *C07D 251/00* | (2006.01) |

(52) U.S. Cl.
USPC .......................................... 514/243; 544/184

(58) Field of Classification Search ................. 514/243; 544/184
See application file for complete search history.

(56) References Cited

U.S. PATENT DOCUMENTS

| 2,837,520 | A | 6/1958 | Fusco et al. |
| 4,209,621 | A | 6/1980 | Dusza et al. |
| 4,405,619 | A | 9/1983 | Heilman et al. |
| 5,236,917 | A | 8/1993 | Dunlap et al. |
| 5,254,548 | A | 10/1993 | Wermuth et al. |
| 7,005,431 | B2 | 2/2006 | Bettati et al. |
| 7,176,203 | B2 | 2/2007 | Chambers et al. |
| 7,767,675 | B2 * | 8/2010 | Zhuo et al. ................ 514/243 |
| 2005/0075340 | A1 | 4/2005 | Zhang et al. |
| 2005/0085473 | A1 | 4/2005 | Van Hirschheydt et al. |
| 2005/0165023 | A1 | 7/2005 | Bettati et al. |
| 2005/0261297 | A1 | 11/2005 | Igarashi et al. |
| 2006/0046991 | A1 | 3/2006 | Cui et al. |
| 2006/0058303 | A1 | 3/2006 | Chambers et al. |
| 2007/0191376 | A1 | 8/2007 | Zou et al. |
| 2008/0039457 | A1 | 2/2008 | Zhuo et al. |
| 2008/0167287 | A1 * | 7/2008 | Zhuo et al. ............. 514/210.18 |
| 2009/0124609 | A1 | 5/2009 | Albrecht et al. |
| 2009/0124612 | A1 | 5/2009 | Albrecht et al. |

FOREIGN PATENT DOCUMENTS

| CA | 1246568 | 12/1988 |
| CA | 2158994 | 9/1994 |
| EP | 430385 | 6/1991 |
| EP | 443453 | 8/1991 |
| EP | 1640010 | 3/2006 |
| FR | 2662163 | 11/1991 |
| JP | 63037347 | 2/1988 |
| JP | 63199347 | 8/1988 |
| JP | 63310891 | 12/1988 |
| JP | 313934 | 1/1991 |
| JP | 4251243 | 9/1992 |
| JP | 5232618 | 9/1993 |
| JP | 2001/043978 | 2/2001 |
| JP | 2001043978 | 2/2001 |
| WO | WO 83/00864 | 3/1983 |
| WO | WO 99/06404 | 2/1999 |
| WO | WO 01/34603 | 5/2001 |
| WO | WO 01/34605 | 5/2001 |
| WO | WO 02/072579 | 9/2002 |
| WO | WO 02079203 | 10/2002 |
| WO | WO 03/080621 | 10/2003 |
| WO | WO 03/087026 | 10/2003 |
| WO | WO 03/097641 | 11/2003 |
| WO | WO 2004/005290 | 1/2004 |
| WO | WO 2004/005291 | 1/2004 |
| WO | WO 2004/020438 | 3/2004 |
| WO | WO 2004/058769 | 7/2004 |
| WO | WO 2004/076412 | 9/2004 |
| WO | WO 2005/004607 | 1/2005 |
| WO | WO 2005/004808 | 1/2005 |
| WO | WO 2005/005378 | 1/2005 |
| WO | WO 2005/010005 | 2/2005 |
| WO | wo 2005/014598 | 2/2005 |
| WO | WO 2005/028475 | 3/2005 |
| WO | WO 2005/030140 | 4/2005 |
| WO | WO 2005/039586 | 5/2005 |
| WO | WO 2005/040154 | 5/2005 |
| WO | WO 2005/040345 | 5/2005 |
| WO | WO 2005/070891 | 8/2005 |
| WO | WO 2005/073224 | 8/2005 |
| WO | WO 2005/077953 | 8/2005 |
| WO | WO 2005/097800 | 10/2005 |
| WO | WO 2005/113494 | 12/2005 |
| WO | WO 2005/121125 | 12/2005 |

(Continued)

OTHER PUBLICATIONS

Fusco R et al: "Ricerche sulle triazine asimmetriche sintesi di derivati tetrazaindenici", Rendiconti Dell'Istituto Lombardo Di Scienze E. Lettere. vol. 88, pp. 194-202 (1958).

(Continued)

*Primary Examiner* — Paul V. Ward
(74) *Attorney, Agent, or Firm* — Lathrop & Gage LLP; Brian C. Trinque

(57) ABSTRACT

The present invention is directed to dihydrochloric acid and dibenzenesulfonic acid salts of the c-Met kinase inhibitor 2-fluoro-N-methyl-4-[7-(quinolin-6-ylmethyl)-imidazo[1,2-b][1,2,4]triazin-2-yl]benzamide, and pharmaceutical compositions thereof, useful in the treatment of cancer and other diseases related to the dysregulation of kinase pathways. The present invention further relates to processes and intermediates for preparing 2-fluoro-N-methyl-4-[7-(quinolin-6-ylmethyl)imidazo[1,2-b][1,2,4]triazin-2-yl]benzamide, and salts thereof.

16 Claims, 5 Drawing Sheets

FOREIGN PATENT DOCUMENTS

| WO | WO 2006/014325 | 2/2006 |
|----|----------------|--------|
| WO | 2006/124354 | 11/2006 |
| WO | WO 2006/124354 | 11/2006 |
| WO | WO 2007/008539 | 1/2007 |
| WO | 2007/015866 A2 | 2/2007 |
| WO | WO 2007/013673 | 2/2007 |
| WO | WO 2007015866 | 2/2007 |
| WO | WO 2007/025090 | 3/2007 |
| WO | WO 2007/064797 | 6/2007 |
| WO | WO 2007/075567 | 7/2007 |
| WO | 2007/096764 | 8/2007 |
| WO | WO 2007/096764 | 8/2007 |
| WO | WO 2008/008539 | 1/2008 |
| WO | 2008/051805 A2 | 5/2008 |
| WO | 2008/064157 A1 | 5/2008 |
| WO | WO 2008/051805 | 5/2008 |
| WO | WO 2008/058126 | 5/2008 |
| WO | WO 2008/144767 | 11/2008 |
| WO | WO 2009/091374 | 7/2009 |

OTHER PUBLICATIONS

Rossi S. et al: "Pigmenti fluorescenti derivati dall' 1,4,7,9-tetrazaindene", chimica E L'Industria, vol. 40, pp. 827-829 (1958).
Tomchin A.B.: "Heterocyclic semicarbazones and thiosemicarbazones. XLV. 1,2,4-Triazinoindole derivatives with a condensed imidazole, thiazole or triazole ring", Journal of Organic Chemistry of the USSR, vol. 18, No. 6, pp. 1103-1110 (1982).
Druzhinin S. U et al: "Acid-Base reactgions of imidazo[1,2,-b]-1,2,4-triazines (imitrines) with proton donors", Russian Journal of General Chemistry, vol. 63, pp. 953-958 (1993).
Kruglenko V.P et al: "Condensed imidazo-1,2,4-azines. Synthesis and transformations of 2-aroylmethyl-6, 7-diphenylimidazo-[1,2-b'-1,2,4-triazin-4H-3-ones", Chemistry of Heterocyclic Compounds (A translation of Khimiya Geterotsiklicheskikh Soedinenii), vol. 34, No. 2, pp. 232-236 (1998).
Acero-Alarcon A et al: "Unusual Ring Closure Reaction of Amides with Pyrimidines: Novel Stereoselective Synthesis of Hexahydroimidazo'1,2-c'pyrimidines", Synthesis, No. 12, pp. 2124-2130 (1999).
Vidal A et al: "Effect of imidazo[1,2-a]pyrimidine derivatives on leukocyte function", Inflammation Research, vol. 50, pp. 317-320 (2001).
Wermuth C G: "Molecular Variations Based on Isosteric Replacements", Practice of Medicinal Chemistry, pp. 203-237 (1996).
International Search Report dated Apr. 11 2008 issued in international application No. PCT/US2007/085100.
Cecil Textbook of Medicine, edited by Bennet, J.D., and Plum F., 20th edition, vol. 1, 1004-1010 (1996).
Freshney et al., Culture of Animal Cells, A Manual of Basic Technique, Alan R. Liss, Inc., p. 4 (1984).
Dermer et al., Bio/Technology, vol. 12, p. 320 (1994).
Cohen et al., Current Opinion in Chemical Biology, vol. 3, pp. 459-465 (1999).
Golub et al., Science, vol. 286, pp. 531-537 (1999).
Mass R.D., Int. J. Radiation Oncology Bio. Phys., vol. 58(3), pp. 932-940 (2004).
Fabbro et al., Pharmacology & Therapeutics, vol. 93, pp. 79-98 (2002).
Brittain, Harry G., "Methods for the Characterization of Polymorphs and Solvates," Polymorphism in Pharmaceutical Solids, Marcel Dekker, Inc., New York, vol. 95, Chpt. 6, pp. 227-278 (1999).
Labouta, Ibrahim M. et al., "Potential antineoplastics: Some subsituted imidazol[1,2-b]-[1,2,4]triazines, triazino[4,3-b][1,2,4]triazines and imidazotriazino[5,6-b]indoles," J. Serb. Chem. Soc., vol. 52(9):523-527 (1987).
International Preliminary Report on Patentability for Application No. PCT/US2009/044622, dated Nov. 23, 2010.
Povstyanoi et al., Izvestiya Timiryazevskoi Sel'skokhozyaistvennoi Akademii (1984),(5),155-9; CA 102: 45885,1985 (CAPLUS Abstract provided).
Labouta et al., Journal of the Serbian Chemical Society (1987), 52(9), 523-7; CA 110:57624, 1989 (CAPLUS Abstract provided).

Cecil Textbook of Medicine, edited by Bennet, J.C., and Plum F., 20th edition, vol. 1, 1004-1010, 1996.
Freshney et al., Culture of Animal Cells, A Manual of Basic Technique, Alan R. Liss, Inc., 1983, New York, p. 4.
Dermer et al., Bio/Technology, 1994, 12:320.
Golub et al., Science, 286, 531-537, 1999.
Mass, R. D., Int. J. Radiation Oncology Bio. Phys. vol. 58(3): 932-940, 2004.
Balkovetz, Daniel, and Lipschutz, Joshua, "Hepatocyte Growth Factor and the Kidney: It Is Not Just for the Liver." Intl. Rev. of Cytology, 186:225-250, 1999.
Birchmeier et al., "Met, Metastasis, Motility, and More." Nature, 4:915-925, Dec. 2003.
Blom et al.. "Preparative LC-MS Purification: Improved Compound-Specific Method Optimization." J. Comb. Chem., 6:874-883, 2004.
Blume-Jensen, Peter, and Hunter, Tony, "Oncogenic kinase signaling." Nature, 411:355-365, May 17, 2001.
Boccaccio, Carla, and Comoglio, Paolo, "Invasive growth: a MET-driven genetic programme for cancer and stem cells." Nature, 6:637-645, Aug. 2006.
Bolen, Joseph, "Nonreceptor tyrosine protein kinases." Oncogene, 8(8):2025-2031, Aug. 1993.
Calic ct al., "Flavonoids as Inhibitors of Lck and Fyn Kinases." Croatica Chemical ACTA., 78(3):367-374, 2005.
Christiansen et al., "c-Met as a target for human cancer and characterization of inhibitors for therapeutic intervention." Cancer Letters, 225:1-26, 2005.
Corso et al., "Cancer therapy: can the challenge be MET?" TRENDS in Molecular Medicine, 11(6):284-292, Jun. 2005.
Crestani et al., "Differential Role of Neutrophils and Aveolar Macrophages in Hepatocyte Growth Factor Production in Pulmonary Fibrosis." Laboratory Investigation, 82(8):1015-1022, Aug. 2002.
Eguchi et al., "Changes in liver regenerative factors in a case of living-related liver transplantation." Clinical Transplantation, 15:536-544, 1999.
Futamatsu et al., "Autoimmune Myocarditis: A Potential Role for Induction of T Helper 2 Hepatocyte Growth Factor Ameliorates the Progression of Experimental Cytokines." Circulation Research, 96:823-830, 2005.
Koch et al., "Hepatocyte Growth Factor." Arthritis and Rheumatism, 39(9):1566-1575, Sep. 1996.
Liu, Youhua, "Hepatocyte growth factor and the kidney." Current Opinion in Nephrology and Hypertension, 11:23-30, 2002.
Ma et al., "Hepatocyte growth factor is a survival factor for endothelial cells and is expressed in human atherosclerotic plaques," Atherosclerosis, 164:79-87, 2002.
Madhusudan, Srinivasan, and Ganesan, Trivadi, "Tyrosine kinase inhibitors in cancer therapy." Clinical Biochemistry, 37:618-635, 2004.
Manning et al., "The Protein Kinase Complement of the Human Genome." Science, 298:1912-1916. 1933-1934, Dec. 6, 2002.
Matsumoto, Kunio. and Nakamura, Toshikazu, "Hepatocyte growth factor: Renotropic role and potential therapeutics for renal diseases." Kidney International, 59:2023-2038, 2001.
Miyazawa et al., "Protection of Hippocampal Neurons from Ischemia-induced Delayed Neuronal Death by Hepatocyte Growth Factor: A Novel Neurotrophic Factor." Journal of Cerebral Blood Flow and Metabolism, 18:345-348, 1998.
Morishita et al., "Therapeutic Angiogenesis using Hepatocyte Growth Factor (HGF)." Current Gear Therapy, 4:199-206, 2004.
Morishita et al., "Hepatocyte Growth Factor as Cardiovascular Hormone: Role of HGF in the Pathogenesis of Cardiovascular Disease." Endocrine Journal, 49(3):273-284, 2002.
Segura-Flores et al., "Factor de crecimiento de hepatocitos (HGF) y sus aplicaciones terapeuticas." Revista de Gastroenterologia de Mexico, 69(4):243-250, Oct.-Dec. 2004.
Wang et al., "Potent and selective inhibitors of the Met [hepatocyte growth factor/scatter factor (HGF/SF) receptor] tyrosine kinase block HGF/SF-induced tumor cell growth and invasion." Molecular Cancer Therapeutics, 2:1085-1092, 2003.

Alarcon et al., "Unusual Ring Closure Reaction of Amides with Pyrimidines: Novel Stereoselective Synthesis of Hexahydroimidazo[1,2-c]pyrimidines." Synthesis, 12:2124-2130, 1999.

Druzhinin et al., "Acid-base Reactions of Imidazo[1,2-b]-1,2,4-Triazines (Imitrines) with Proton Donors." Russian Journal of General Chemistry, 63(6):953-958, 1993.

Fusco, Raffaelo, and Rossi, Silvan, "Ricerche Sulle Triazine Assimetriche Sintesi Di Derivati Tetraziandenici," Rendiconti, 88:194-202, 1955.

Kruglenko et al., "Condensed Imidazo-1,2,4-azines. 28. Synthesis and Transformations of 2-Aroylmethyl-6,7-Diphenylimidazo-[1,2-b]-1,2,4-Triazin-4H-3-Ones." Chemistry of Heterocyclic Compounds, 34(2):232-236, 1998.

Labouta et al., "Potential Antineoplastics: Some Substituted Imidazo[1,2-b][1,2,4]triazines,[4,3-b][1,2,4]triazines and imidazotriazino-[5,6-b]indoles." Journal of the Serbian Chemical Society, 52(9):523-527, 1987.

Rossi, Silvan, and Trave, Roberto, "Pigmenti Fluorescenti derivati dall'1,4,7,9—tetraziandene." La Chimica E L 'Industria. 40(10):827-830, Oct. 1958.

Tomchin A. B., Heterocyclic Semicarbazones and Thiosemicarbazones. XLV. 1,2,4-Triazinoindole Derivatives with a Condensed Imidazole, Thiazole, or Thiazole Ring. Journal of Organic Chemistry of the USSR, 18(6):1272-1280, Jun. 1982.

Vidal et al., "Effect of imidazo[1,2-a]pyrimidine derivatives on leukocyte function." Inflammation Research, 50:317-320, 2000.

Wermuth, Camille, "Molecular Variations Based on Isosteric Replacements." The Practice of Medical Chemistry, 203-237, 1996. XP002190259, chap. IID.

International Search Report for PCT/US2007085100, Sebastian, dated Apr. 11, 2008.

Liu, X, "INCB28060 A Novel, Potent and Selective c-MET RTK Inhibitor for Cancer Treatment" presented at GTC Bio: The 4.sup.th Modern Drug Discovery & Development Summit, San Diego, CA, Oct. 15-17, 2008.

STN search dated Oct. 16, 2006.

Liu, X. "Discovery and Characterization of INCB028060: A Novel, Potent and Selective MET RTK Inhibitor for Cancer Treatment," presentation at the AACR Annual Meeting, Apr. 12-16, 2008.

Abdel-Rahman, R. M.; Seada, M.; Fawzy, M.; El-Baz, Ibrahim, "Synthesis of some new thioethers of 1,2,4-triazine-3-hydrazones and assays for their anticancer and antihuman immune virus activities," Farmaco (1993), 48(3), 397-406, CODEN: FRMCE8; ISSN: 0014-827X.

Cohen et al., "The development and therapeutic potential of protein kinase inhibitors," Current Opinion in Chemical Biology, 459-465, 1999.

Fabbro et al., "Protein Kinases as Targets for Anticancer Agents: from Inhibitors to Useful Drugs", Pharmacology & Therapeutics 93 pp. 79-98 (2002).

Holla, B. Shivarama; Sarojini, B. K; Rao, B.,Sooryanarayana; Poojary, Boja, "Synthesis and reactions of new N-bridged heterocycles derived from 3-substituted-4,5-diamino-1,2,4-triazoles," Indian Journal of Chemistry, Section B: Organic Chemistry Including Medicinal Chemistry (2003),42B(9), 2054-2058.

International Preliminary Report on Patentability for PCT/US20071075254, dated Feb. 10, 2009.

International Preliminary Report on Patentability for PCT/US20071085100, Jun. 4, 2009.

International Search Report for PCT/US2007/075254, Jan. 18, 2008.

Koblish, H.K. et al., "Preclinical in vivo characteristic of INCB028060, a novel, potent and highly selective c-Met inhibitor," J. Clinical Oncology,2008 ASCO Annual Meeting Proceedings (Post-Meeting Edition). vol. 26, No. 15S (May 20 Supplement), 2008: 14561.

Krayushkin, M. M.; Yarovenko, V. N.; Sedishev, I. P.; Zavarzin, I. V.; Vorontsova, L. G.; Starikova, Z. A., "Synthesis and Structure of 5-Indolyl-6-thienyl-1,2,4-Triazines," Russian Journal of Organic Chemistry (2005), 41(6), 875-883, CODEN: RJOCEQ; ISSN: 1070-4280.

Journal of Organic Chemistry (2005), 41(6), 875-883, CODEN: RJOCEQ; ISSN: 1070-4280.

Liu, X., "Targeting the c-Met signaling pathway for cancer treatment," Expert Opin. Investig. Drugs (2008) 17(7) 997-1011.

Russian Journal of Organic Chemistry (2005), 41(6), 875-883, CODEN: RJOCEQ; ISSN: 1070-4280.

STN search report (Registry file compounds, Jul. 26, 2006).

STN search report (Registry file compounds, Oct. 19, 2006).

STN search report (Registry file compounds, Nov. 1, 2006).

Fusco, Raffaelo, and Rossi, Silvan, "Ricerche Sulle Triazine Assimetriche Sintesi Di Derivati Tetraziandenici," Rendiconti, 88:194-202 (1955)(English translation).

Rossi, Silvan, and Trave, Roberto, "Pigmenti Fluorescenti derivati dall'1,4,7,9—tetraziandene." La Chimica E L'Industria. 40(10):827-830 (Oct. 1958)(English translation).

Berge et al. Journal of Pharmaceutical Sciences, vol. 66, No. 1, Jan. 1977, 1-19.

Monatshefte fuer Chemie (1988), 119(5), 591-6, CODEN: MOCMB7; ISSN: 0026-9247.

Remington's Pharmaceutical Sciences, 17.sup.th ed., Mack Publishing Company, Easton, PA., 1985, p. 1418.

\* cited by examiner

SALTS OF 2-FLUORO-N-METHYL-4-[7-(QUINOLIN-6-YL-METHYL)-IMIDAZO[1,2-B][1,2,4]TRIAZIN-2-YL]BENZAMIDE AND PROCESSES RELATED TO PREPARING THE SAME

CROSS REFERENCE TO RELATED APPLICATIONS

This application claims priority to U.S. Ser. No. 61/054,995, filed May 21, 2008, which is incorporated herein by reference in its entirety

FIELD OF THE INVENTION

The present invention is directed to dihydrochloric acid and dibenzenesulfonic acid salts of the kinase inhibitor 2-fluoro-N-methyl-4-[7-(quinolin-6-ylmethyl)imidazo[1,2-b][1,2,4]triazin-2-yl]benzamide, useful in the treatment of cancer and other diseases related to the dysregulation of kinase pathways. The present invention further relates to processes and intermediates for preparing 2-fluoro-N-methyl-4-[7-(quinolin-6-ylmethyl)imidazo[1,2-b][1,2,4]triazin-2-yl]benzamide, and salts thereof.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

c-Met, a proto-oncogene, is a member of a distinct subfamily of heterodimeric receptor tyrosine kinases which include Met, Ron, and Sea (Birchmeier, C. et al., Nat. Rev. Mol. Cell Biol. 2003, 4(12):915-925; Christensen, J. G. et al., Cancer Lett. 2005, 225(1):1-26). The only high affinity ligand for c-Met is the hepatocyte growth factor (HGF), also known as scatter factor (SF). Binding of HGF to c-Met induces activation of the receptor via autophosphorylation resulting in an increase of receptor dependent signaling. Both c-Met and HGF are widely expressed in a variety of organs, but their expression is normally confined to the cells of epithelial and mesenchymal origin, respectively. The biological functions of c-Met (or c-Met signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

HGF and c-Met are each required for normal mammalian development, and abnormalities reported in both HGF- and c-Met-null mice are consistent with proximity of embryonic expression and epithelial-mesenchymal transition defects during organ morphogenesis (Christensen, J. G. et al., Cancer Lett. 2005, 225(1):1-26). Consistent with these findings, the transduction of signaling and subsequent biological effects of HGF/c-Met pathway have been shown to be important for epithelial-mesenchymal interaction and regulation of cell migration, invasion, cell proliferation and survival, angiogenesis, morphogenesis and organization of three-dimensional tubular structures (e.g. renal tubular cells, gland formation) during development. The specific consequences of c-Met pathway activation in a given cell/tissue are highly context-dependent.

Dysregulated c-Met pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1):1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. In addition to the abnormal HGF/c-Met expression, c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement, as well as abnormal receptor processing and defective negative regulatory mechanisms.

The various cancers in which c-Met is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-Met pathway contributes to tumor formation and progression and could be a good target for effective cancer intervention has been further solidified by numerous preclinical studies (Birchmeier, C. et al., Nat. Rev. Mol. Cell Biol. 2003, 4(12):915-925; Christensen, J. G. et al., Cancer Lett. 2005, 225(1):1-26; Corso, S. et al., Trends in Mol. Med. 2005, 11(6):284-292). For example, studies showed that the tpr-met fusion gene, overexpression of c-met and activated c-met mutations all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-Met signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/c-Met signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

Inhibitors of c-Met and other kinases are reported in U.S. Ser. No. 11/942,130, including the compound 2-fluoro-N-methyl-4-[7-(quinolin-6-ylmethyl)imidazo[1,2-b][1,2,4]triazin-2-yl]benzamide (I) having the structure indicated below.

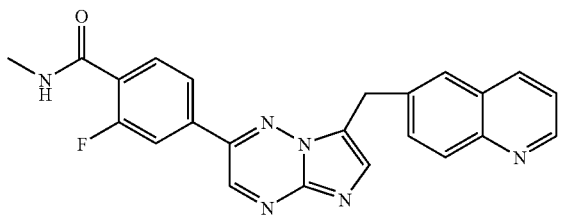

(I)

New or improved forms of existing agents which inhibit kinases such as c-Met are continually needed for developing more effective pharmaceuticals to treat cancer and other diseases. The salts, compositions, and methods described herein are directed toward these needs and other ends.

SUMMARY OF THE INVENTION

The present invention provides a salt which is 2-fluoro-N-methyl-4-[7-(quinolin-6-ylmethyl)imidazo[1,2-b][1,2,4]triazin-2-yl]benzamide dihydrochloric acid salt, or a hydrate or solvate thereof.

The present invention further provides a salt which is 2-fluoro-N-methyl-4-[7-(quinolin-6-ylmethyl)imidazo[1,2-b][1,2,4]triazin-2-yl]benzamide dibenzensulfonic acid salt, or a hydrate or solvate thereof.

The present invention further provides compositions comprising a salt of the invention, or a hydrate or solvate thereof, and at least one pharmaceutically acceptable carrier.

The present invention further provides methods of inhibiting activity of a receptor or non-receptor tyrosine kinase comprising contacting a kinase with a salt of the invention, or a hydrate or solvate thereof.

The present invention further provides methods of inhibiting the HGF/c-Met kinase signaling pathway in a cell comprising contacting the cell with a salt of the invention, or a hydrate or solvate thereof.

The present invention further provides methods of inhibiting the proliferative activity of a cell comprising contacting the cell with a salt of the invention, or a hydrate or solvate thereof.

The present invention further provides methods of inhibiting tumor growth in a patient comprising administering to the patient a therapeutically effective amount of a salt of the invention, or a hydrate or solvate thereof.

The present invention further provides methods of inhibiting tumor metastasis in a patient comprising administering to the patient a therapeutically effective amount of a salt of the invention, or a hydrate or solvate thereof.

The present invention further provides methods of treating a disease in a patient, wherein the disease is associated with dysregulation of the HGF/c-MET signaling pathway, comprising administering to the patient a therapeutically effective amount of a salt of the invention, or a hydrate or solvate thereof.

The present invention further provides methods of treating a cancer in a patient comprising administering to the patient a therapeutically effective amount of a salt of the invention, or a hydrate or solvate thereof.

The present invention further provides processes of preparing a dihydrochloric acid salt of 2-fluoro-N-methyl-4-[7-(quinolin-6-ylmethyl)imidazo[1,2-b][1,2,4]triazin-2-yl]benzamide, comprising:

a) reacting a first mixture comprising 2-fluoro-N-methyl-4-[7-(quinolin-6-ylmethyl)imidazo[1,2-b][1,2,4]triazin-2-yl]benzamide and water with at least two equivalents of hydrochloric acid in a solvent comprising water to form a second mixture; and b) combining the second mixture with methyl tert-butyl ether.

The present invention further provides processes of preparing a dihydrochloric acid salt of 2-fluoro-N-methyl-4-[7-(quinolin-6-ylmethyl)imidazo[1,2-b][1,2,4]triazin-2-yl]benzamide, comprising:

a) reacting a first mixture comprising 2-fluoro-N-methyl-4-[7-(quinolin-6-ylmethyl)imidazo[1,2-b][1,2,4]triazin-2-yl]benzamide and methanol with at least two equivalents of hydrochloric acid in a solvent comprising isopropanol to form a second mixture; and b) combining the second mixture with acetone.

The present invention further provides processes of preparing a dibenzenesulfonic acid salt of 2-fluoro-N-methyl-4-[7-(quinolin-6-ylmethyl)imidazo[1,2-b][1,2,4]triazin-2-yl]benzamide, comprising:

a) reacting a first mixture comprising 2-fluoro-N-methyl-4-[7-(quinolin-6-ylmethyl)imidazo[1,2-b][1,2,4]triazin-2-yl]benzamide and methanol with at least two equivalents of benzenesulfonic acid in a solvent comprising isopropanol to form a second mixture; and b) combining the second mixture with methyl tert-butyl ether.

The present invention further provides processes of preparing a compound of Formula I:

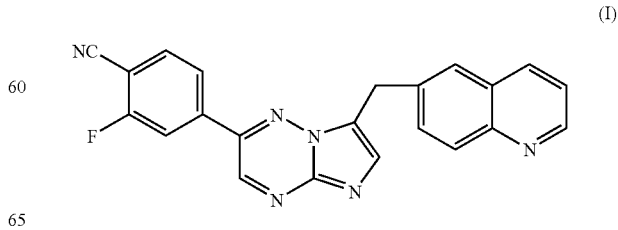

(I)

or salt thereof;

comprising reacting a compound of Formula II:

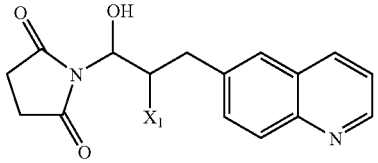

with a compound of Formula III:

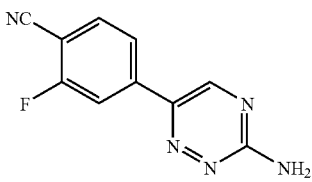

to form a compound of Formula I, or salt thereof;

wherein $X_1$ is chloro, bromo, or iodo.

The present invention further provides processes of preparing a compound of Formula I:

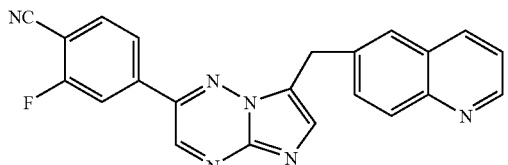

comprising:

a) reacting a compound of Formula II:

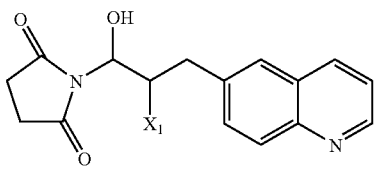

with a compound of Formula VII:

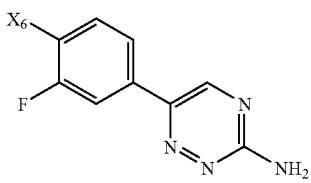

to form a compound of Formula VI:

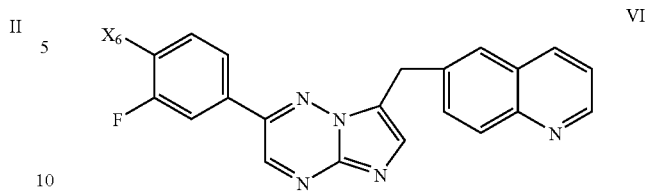

and b) reacting the compound the compound of Formula VI with $Zn(CN)_2$ and Zn in the presence of a catalyst.

wherein $X_6$ is chloro, bromo, or iodo.

The present invention further provides compounds of Formula III:

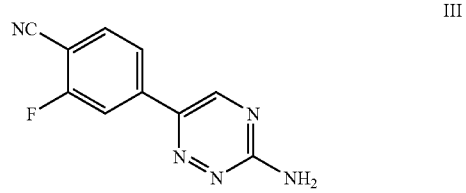

or salts thereof.

The present invention further provides compounds of Formula II:

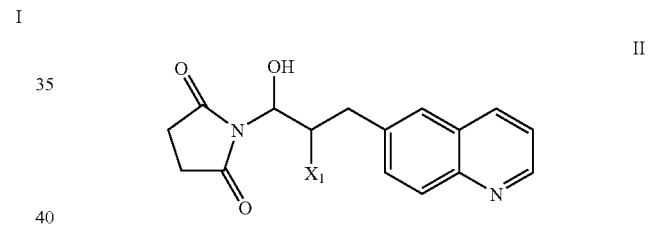

wherein $X^1$ is chloro, iodo, or bromo.

DETAILED DESCRIPTION

The present invention provides, inter alia, dihydrochloric acid and dibenzenesulfonic acid salts of the c-Met kinase inhibitor 2-fluoro-N-methyl-4-[7-(quinolin-6-ylmethyl)-imidazo[1,2-b][1,2,4]triazin-2-yl]benzamide (see Formula I above). The salts of the invention are advantageous in that they can be obtained in crystalline form, making them particularly suitable for use in pharmaceutical formulations.

Dihydrochloric Acid Salt

Figure 1:
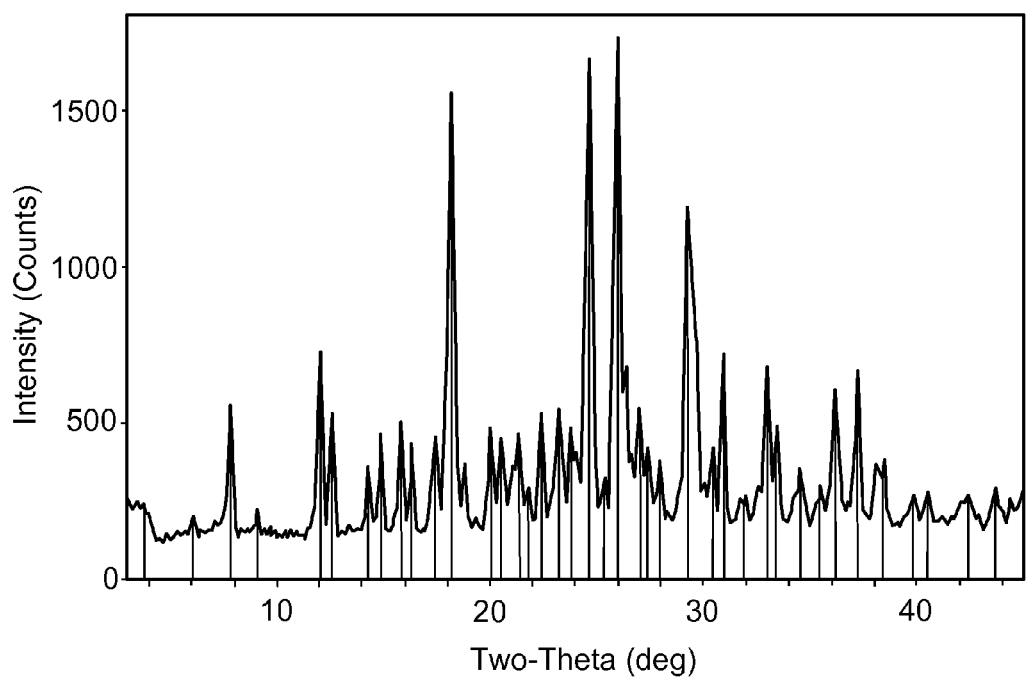
FIG. 1 shows an X-ray powder diffraction (XRPD) pattern characteristic of a dihydrochloric acid salt of the invention prepared according to the process of Example 1.

The dihydrochloric acid salt can be prepared by combining 2-fluoro-N-methyl-4-[7-(quinolin-6-ylmethyl)-imidazo[1,2-b][1,2,4]triazin-2-yl]benzamide with a molar excess of hydrochloric acid, such as described in Example 1 below. The dihydrochloric acid salt can be obtained as a crystalline solid as evidenced by the XRPD pattern shown in FIG. 1 (see also Example 2 below). The dihydrochloric acid salt can also be obtained as a hydrate, based on the TGA results shown in FIG. 3 (see also Example 4 below). DSC indicates that the dihydrochloric acid salt melts at about 220 to about 224° C., or more particularly at about 222° C. (see FIG. 2 and Example 3). The solubility at 25° C. was found to be approximately 4.5 mg/mL in water; 0.002 mg/mL in pH 7.4 buffer; 0.002 mg/mL in pH 8.0 buffer; and approximately 24 mg/mL in 0.1 N aqueous HCl. The salt prepared by the method of Example 1 was found to be desirably reproducible with good solubility properties.

In some embodiments, the dihydrochloride salt has an X-ray powder diffraction pattern comprising a characteristic peak expressed in degrees 2θ at about 26.0. In some embodiments, the dihydrochloride salt has an X-ray powder diffraction pattern comprising a characteristic peak expressed in degrees 2θ at about 24.7. In some embodiments, the dihydrochloride salt has an X-ray powder diffraction pattern comprising a characteristic peak expressed in degrees 2θ at about 18.2. In some embodiments, the dihydrochloride salt has an X-ray powder diffraction pattern comprising a characteristic peak expressed in degrees 2θ at about 29.3. In some embodiments, the dihydrochloride salt has an X-ray powder diffraction pattern comprising characteristic peaks expressed in degrees 2θ at about 26.0 and 24.7. In some embodiments, the dihydrochloride salt has an X-ray powder diffraction pattern comprising a characteristic peak expressed in degrees 2θ at about 7.8. In some embodiments, the dihydrochloride salt has an X-ray powder diffraction pattern comprising characteristic peaks expressed in degrees 2θ at about 26.0, 24.7, 18.2, and 29.3. In some embodiments, the dihydrochloride salt has an X-ray powder diffraction pattern comprising a characteristic peak expressed in degrees 2θ at about 7.8, 26.0, 24.7, 18.2, and 29.3.

Dibenzenesulfonic Acid Salt

Figure 4:
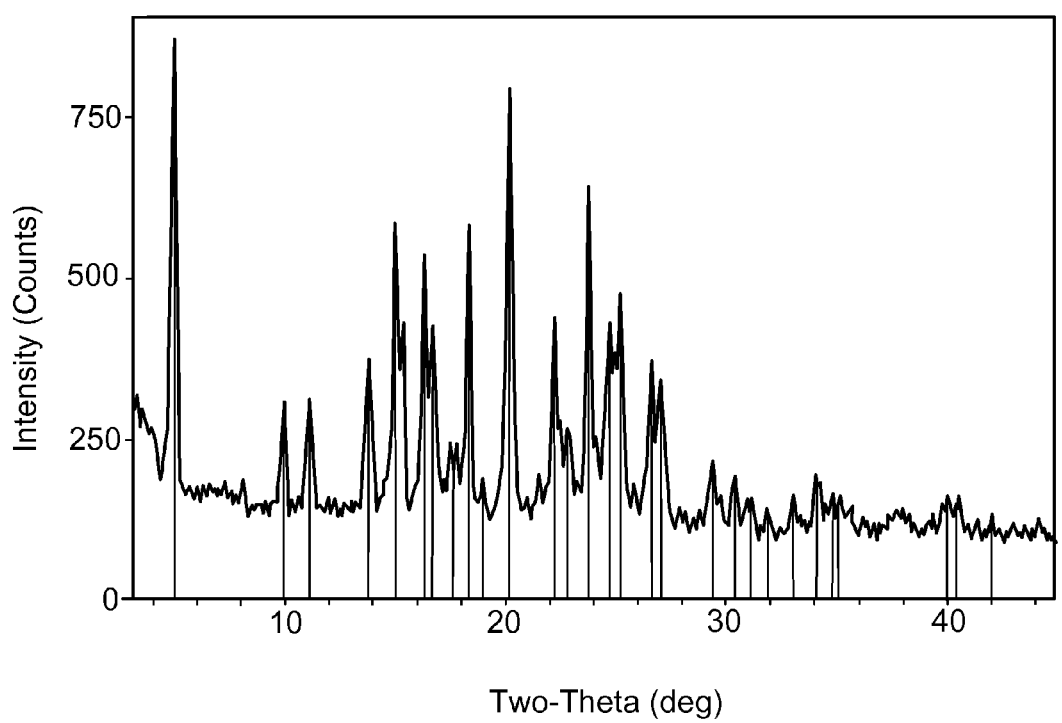
FIG. 4 shows an X-ray powder diffraction (XRPD) pattern characteristic of a dibenzenesulfonic acid salt of the invention prepared according to the process of Example 5.

The dibenzenesulfonic acid salt (di-besylate salt) can be prepared by combining 2-fluoro-N-methyl-4-[7-(quinolin-6-ylmethyl)-imidazo[1,2-b][1,2,4]triazin-2-yl]benzamide with a molar excess of benzenesulfonic acid, such as described in Example 5 below. The dibenzenesulfonic acid salt can be obtained as a crystalline solid as evidenced by the XRPD pattern shown in FIG. 4 (see also Example 5 below). DSC indicates that the dibenzenesulfonic acid salt melts at about 268 to about 272° C., or more particularly at about 270° C. (see FIG. 5 and Example 7). The solubility at 25° C. was found to be approximately 3.9 mg/mL in water; 0.003 mg/mL in pH 7.4 buffer; 0.003 mg/mL in pH 8.0 buffer; and at least 29 mg/mL in 0.1 N aqueous HCl.

In some embodiments, the present invention provides a particular form of the dibenzensulfonate salt having an X-ray powder diffraction pattern comprising a characteristic peak expressed in degrees 2θ at about 20.2. In some embodiments, the dibenzensulfonate salt has an X-ray powder diffraction pattern comprising a characteristic peak expressed in degrees 2θ at about 15.0. In some embodiments, the dibenzensulfonate salt has an X-ray powder diffraction pattern comprising a characteristic peak expressed in degrees 2θ at about 16.3. In some embodiments, the dibenzensulfonate salt has an X-ray powder diffraction pattern comprising a characteristic peak expressed in degrees 2θ at about 18.3. In some embodiments, the dibenzensulfonate salt has an X-ray powder diffraction pattern comprising a characteristic peak expressed in degrees 2θ at about 23.8. In some embodiments, the dibenzensulfonate salt has an X-ray powder diffraction pattern comprising a characteristic peak expressed in degrees 2θ at about 4.9. In some embodiments, the dibenzensulfonate salt has an X-ray powder diffraction pattern comprising characteristic peaks expressed in degrees 2θ at about 15.0, 16.3, 18.3, 20.2, and 23.8. In some embodiments, the dibenzensulfonate salt has an X-ray powder diffraction pattern comprising characteristic peaks expressed in degrees 2θ at about 15.0, 16.3, 18.3, 20.2, 23.8, and 4.9.

Definitions and Additional Embodiments

The present invention includes hydrates or solvates of the above-recited salts. Solvates refer to salts containing solvent within or as a component of the crystalline lattice. The term "hydrate," as used herein, is a particular solvate where the solvent is water and is meant to refer to a substance having waters of hydration. Example hydrates include hemihydrates, monohydrates, dihydrates, etc.

In some embodiments, the salts of the invention are crystalline. As used here in, a "crystalline" substance refers to a substance that contains at least some crystalline material. The presence of crystalline material can be detected by way of XRPD, for example. The salts of the invention might crystallize in different crystalline forms having different crystalline lattices and, consequently, have different physical properties. Some crystalline forms may have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as a salt of the invention, can include both anhydrous forms of that substance and solvated/hydrated forms of that substance, where each of the anhydrous forms and solvated/hydrated forms are distinguished from each other by different XRPD patterns, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a solid or crystalline form reported herein having a DSC thermogram "substantially" as shown in any of the Figures is understood to accommodate such variation.

The salt of the invention can also include all isotopes of atoms occurring in the salt. Isotopes include those atoms having the same atomic number but different mass numbers. For example, isotopes of hydrogen include tritium and deuterium.

The salt of the invention, and its solid forms, can be found together with other substances or can be isolated. In some embodiments, the salt of the invention, or its sold forms, is substantially isolated. By "substantially isolated" is meant that the salt is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the salt of the invention. Methods for isolating compounds and their salts are routine in the art.

Methods

Treatment of a cell (in vitro or in vivo) that expresses a protein kinase with the salt of the invention can result in inhibiting the ligand/kinase signaling pathway and inhibiting downstream events related to the signaling pathway such as cellular proliferation and increased cell motility. For example, the salt of the invention can block and/or impair the biochemical and biological processes resulting from c-Met pathway activation, including, but not limited to, c-Met kinase activation (e.g. c-Met phosphorylation) and signaling (activation and recruitment of cellular substrates such as Gab1, Grb2, Shc and c-Cbl and subsequent activation of a number of signal transducers including PI-3 kinase, PLC-γ, STATs, ERK1/2 and FAK), cell proliferation and survival, cell motility, migration and invasion, metastasis, angiogenesis, and the like. Thus, the present invention further provides methods of inhibiting a ligand/kinase signaling pathway such as the HGF/c-Met kinase signaling pathway in a cell by contacting the cell with a salt of the invention. The present invention further provides methods of inhibiting proliferative activity of a cell or inhibiting cell motility by contacting the cell with a salt of the invention.

The present invention further provides methods of treating diseases associated with a dysregulated kinase signaling pathway, including abnormal activity and/or overexpression of the protein kinase, in an individual (e.g., patient) by administering to the individual in need of such treatment a therapeutically effective amount or dose of a salt of the present invention or a pharmaceutical composition thereof. In some embodiments, the dysregulated kinase is of the Met family (e.g., c-Met, Ron, or Sea). In some embodiments, the dysregulated kinase is overexpressed in the diseased tissue of the patient. In some embodiments, the dysregulated kinase is abnormally active in the diseased tissue of the patient. Dysregulation of c-Met and the HGF/c-Met signaling pathway is meant to include activation of the enzyme through various mechanisms including, but not limited to, HGF-dependent autocrine and paracrine activation, c-met gene overexpression and amplification, point mutations, deletions, truncations, rearrangement, as well as abnormal c-Met receptor processing and defective negative regulatory mechanisms.

In some embodiments, the salt of the invention is useful in treating diseases such as cancer, atherosclerosis, lung fibrosis, renal fibrosis and regeneration, liver disease, allergic disorder, inflammatory disease, autoimmune disorder, cerebrovascular disease, cardiovascular disease, or condition associated with organ transplantation. In further embodiments, the compounds of the invention can be useful in methods of inhibiting tumor growth or metastasis of a tumor in a patient.

Example cancers treatable by the methods herein include bladder cancer, breast cancer, cervical cancer, cholangiocarcinoma cancer, colorectal cancer, esophageal cancer, gastric cancer, head and neck cancer, cancer of the kidney, liver cancer, lung cancer, nasopharygeal cancer, ovarian cancer, pancreatic cancer, prostate cancer, thyroid cancer, osteosarcoma, synovial sarcoma, rhabdomyosarcoma, MFH/fibrosarcoma, leiomyosarcoma, Kaposi's sarcoma, multiple myeloma, lymphoma, adult T cell leukemia, acute myelogenous leukemia, chronic myeloid leukemia. glioblastoma, astrocytoma, melanoma, mesothelioma, or Wilm's tumor, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a compound of the invention with a protein kinase includes the administration of a compound of the present invention to an individual or patient, such as a human, as well as, for example, introducing a compound of the invention into a sample containing a cellular or purified preparation of the protein kinase.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapy

One or more additional pharmaceutical agents or treatment methods such as, for example, chemotherapeutics, anti-cancer agents, cytotoxic agents, or anti-cancer therapies (e.g., radiation, hormone, etc.), can be used in combination with the salt of the present invention for treatment of the diseases, disorders or conditions described herein. The agents or therapies can be administered together with the salt of the invention (e.g., combined into a single dosage form), or the agents or therapies can be administered simultaneously or sequentially by separate routes of administration.

Suitable anti-cancer agents include kinase inhibiting agents including trastuzumab (Herceptin), imatinib (Gleevec), gefitinib (Iressa), erlotinib hydrochloride (Tarceva), cetuximab (Erbitux), bevacizumab (Avastin), sorafenib (Nexavar), sunitinib (Sutent), and RTK inhibitors described in, for example, WO 2005/004808, WO 2005/004607, WO 2005/005378, WO 2004/076412, WO 2005/121125, WO 2005/039586, WO 2005/028475, WO 2005/040345, WO 2005/039586, WO 2003/097641, WO 2003/087026, WO 2005/040154, WO 2005/030140, WO 2006/014325, WO 2005/070891, WO 2005/073224, WO 2005/113494, and US Pat. App. Pub. Nos. 2005/0085473, 2006/0046991, and 2005/0075340.

Suitable chemotherapeutic or other anti-cancer agents further include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents further include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.). Further antibody therapeutics include antibodies to tyrosine kinases and/or their ligands such as anti-HGF antibodies and/or anti-c-Met antibodies. The term "antibody" is meant to include whole antibodies (e.g., monoclonal, polyclonal, chimeric, humanized, human, etc.) as well as antigen-binding fragments thereof.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Other anti-cancer agents include anti-cancer vaccines such as dendritic cells, synthetic peptides, DNA vaccines and recombinant viruses.

Methods for the safe and effective administration of most of the above agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Intermediates and Processes

In some embodiments, the present invention provides a process of preparing a particular form of the dihydrochloride salt by a process comprising:

a) reacting a first mixture comprising 2-fluoro-N-methyl-4-[7-(quinolin-6-ylmethyl)imidazo[1,2-b][1,2,4]triazin-2-yl]benzamide and water with at least two equivalents of hydrochloric acid in a solvent comprising water to form a second mixture; and b) combining the second mixture with methyl tert-butyl ether.

In some embodiments, step a) is carried out at a temperature of about 20 to about 30° C.

In some embodiments, step a) and b) are carried out at about room temperature.

In some embodiments, the present invention provides a process of preparing a particular form of the dihydrochloride salt by a process comprising:

a) reacting a first mixture comprising 2-fluoro-N-methyl-4-[7-(quinolin-6-ylmethyl)imidazo[1,2-b][1,2,4]triazin-2-yl]benzamide and methanol with at least two equivalents of hydrochloric acid in a solvent comprising isopropanol to form a second mixture; and b) combining the second mixture with acetone.

In some embodiments, step a) and b) are carried out at a temperature of about 50 to about 60° C.

In some embodiments, step a) and b) are carried out at a temperature of about 55° C.

In some embodiments, the present invention provides a process of preparing a particular form of the dibenzensulfonic acid salt, comprising:

a) reacting a first mixture comprising 2-fluoro-N-methyl-4-[7-(quinolin-6-ylmethyl)imidazo[1,2-b][1,2,4]triazin-2-yl]benzamide and methanol with at least two equivalents of benzenesulfonic acid in a solvent comprising isopropanol; and b) combining the second mixture with methyl tert-butyl ether.

In some embodiments, step a) and b) are carried out at a temperature of about 50 to about 60° C. In some embodiments, step a) and b) are carried out at a temperature of about 55° C.

The present invention also provides, inter alia, processes and intermediates useful in the preparation of 2-fluoro-N-methyl-4-[7-(quinolin-6-ylmethyl)-imidazo[1,2-b][1,2,4]triazin-2-yl]benzamide and the salts thereof, including the salts of the invention.

For example, in some embodiments, the present invention provides a compound of Formula III:

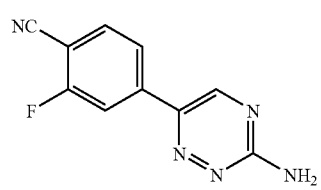

or salt thereof.

The present invention also provides a compound of Formula II:

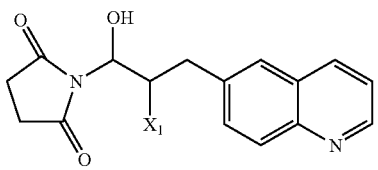

wherein $X^1$ is chloro, iodo, or bromo.

In some embodiments, $X_1$ is chloro.

The present invention further provides a process of preparing a compound of Formula I:

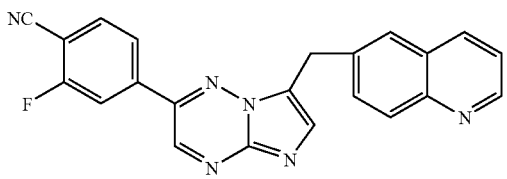

or salt thereof;
comprising reacting a compound of Formula II:

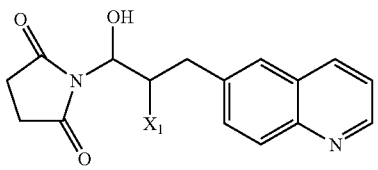

with a compound of Formula III:

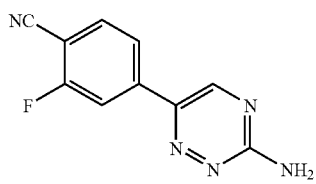

to form a compound of Formula I, or salt thereof;
wherein $X_1$ is chloro, bromo, or iodo.

In some embodiments, $X_1$ is chloro.

In some embodiments, the reacting is carried out in a solvent such as ethylene glycol. In some embodiments, the reaction is conducted at a temperature of from about 120° C. to about 150° C., or from about 130° C. to about 140° C. In some embodiments, the reacting is carried out for about three to about four hours.

In some embodiments, the process further comprises reacting the compound of Formula I, or salt thereof, with a strong acid to form compound of Formula IV:

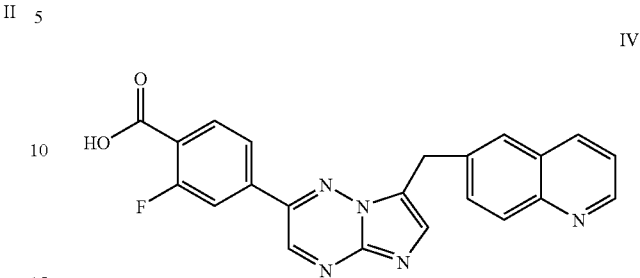

or salt thereof.

In some embodiments, the acid is hydrochloric or hydrobromic acid. In some embodiments, the acid is concentrated hydrochloric acid.

In some embodiments, the reacting of the compound of Formula I with a strong acid is carried out at a temperature of from about 80° C. to about 120° C., from about 90° C. to about 110° C., or about 100° C. In some embodiments, the reacting is carried out for about 15 to about 24 hours, or about 18 hours.

In some embodiments, the process further comprises reacting the compound of Formula IV, or salt thereof, with $CH_3NH_2$ in the presence of at least one coupling agent to form a compound of Formula V:

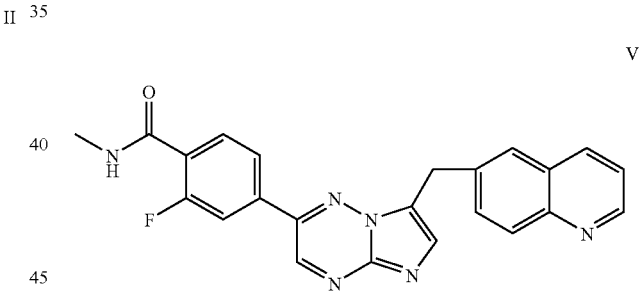

or salt thereof.

In some embodiments, the coupling agent is selected from 1-ethyl-3-(3-dimethylaminopropyl)carbodiimide (EDC), N-hydroxybenzotriazole (HOBt), (benzotriazol-1-yloxyl) tripyrrolidinophosphonium hexaflurophosphate (PyBOP), and salts thereof.

In some embodiments, the reacting of the compound of Formula IV with $CH_3NH_2$ is carried out at a temperature of from about 15° C. to about 40° C., from about 15° C. to about 25° C., about 30° C., or about room temperature. In some embodiments, the reacting is carried out in a solvent, including, but not limited to, acetonitrile. In some embodiments, the reacting is carried out in the presence of a base, including, but not limited to, a tertiary amine, such as triethylamine. In some embodiments, the $CH_3NH_2$ is present in an amount of about 1 to about 10 equivalents, about 2 to about 8 equivalents, or about 3 to about 6 equivalents.

In some embodiments, the process further comprises:
a) reacting the compound of Formula IV:

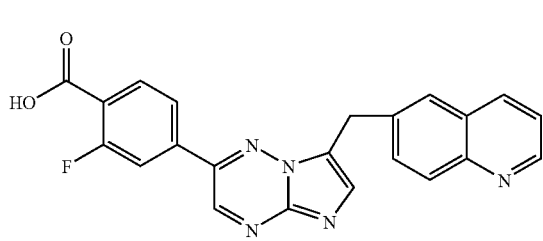

IV or salt thereof, with a halogenating agent, to form a compound of Formula VI:

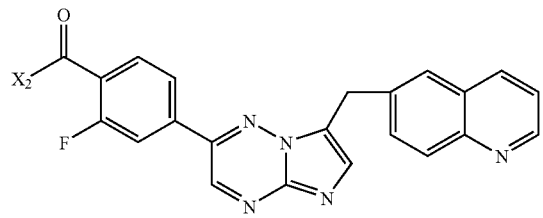

VI or salt thereof; and
b) reacting the compound of Formula VI, or salt thereof, with $CH_3NH_2$ to form a compound of Formula V:

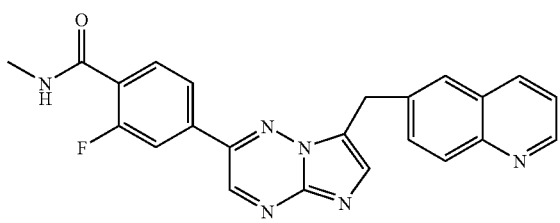

V or salt thereof; wherein $X_2$ is halogen.

In some embodiments, $X_2$ is chloro. In some embodiments, the halogenating agent is thionyl chloride. In some embodiments, the halogenating agent is oxalyl chloride.

In some embodiments, the reacting of the compound of Formula IV with a halogenating agent is carried out at a temperature of from about 50° C. to about 80° C., from about 60° C. to about 75° C., or about 72° C. In some embodiments, the reacting is carried out in a solvent, including, but not limited to, toluene. In some embodiments, the halogenating agent is present in an amount of about 1 to about 20 equivalents, about 8 to about 12 equivalents, or about 10 equivalents.

In some embodiments, the reacting of the compound of Formula VI with $CH_3NH_2$ is carried out at a temperature of from about 0° C. to about 35° C., from about 0 to about 10° C., or about room temperature. In some embodiments, the reacting is carried out in a solvent, including, but not limited to, tetrahydrofuran. In some embodiments, the $CH_3NH_2$ is present in an amount of about 1 to about 20 equivalents, about 8 to about 12 equivalents, or about 10 equivalents.

In some embodiments, step b) is carried out in the presence of a base (e.g., a tertiary amine).

In some embodiments, the process further comprises preparing the compound of Formula II:

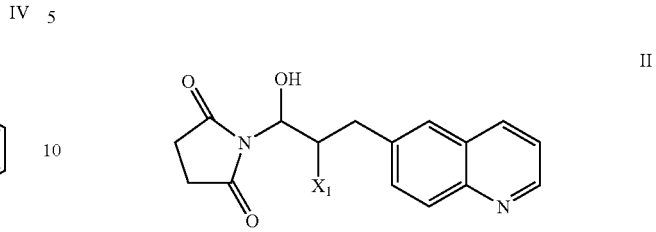

II by a process comprising reacting a compound of Formula IIa:

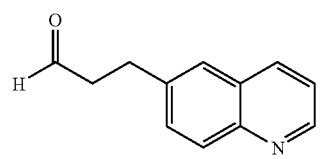

IIa with a compound of Formula IIb:

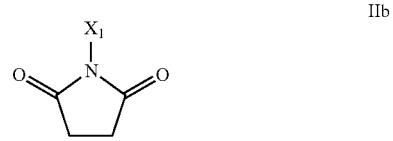

IIb wherein $X_1$ is chloro, bromo, or iodo.

In some embodiments, $X_1$ is chloro.

In some embodiments, the reacting is carried out in the presence of proline. In some embodiments, the reacting is carried out in the presence of proline and benzoic acid. In some embodiments, the reacting of the compound of Formula IIa with the compound of Formula IIb is carried out at a temperature of from about 0° C. to about 50° C., from about 20° C. to about 40° C., or about 20° C. In some embodiments, the reacting is carried out in a solvent, including, but not limited to, methylene chloride. In some embodiments, the compound of Formula IIb is present in an amount of about 1 to about 2 equivalents, about 1 to about 1.5 equivalents, about 1 to about 1.2 equivalents, or about 1.05 equivalents. In some embodiments, proline is present in an amount of about 0.1 to about 0.5 equivalents, or about 0.1 to about 0.2 equivalents. In some embodiments, proline is present in an amount of about 0.1 equivalents and benzoic acid is present in an amount of about 0.1 equivalents.

In some embodiments, the process further comprises preparing the compound of Formula IIa by a process comprising reacting a compound of Formula IIc:

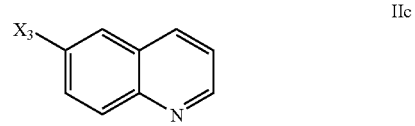

IIc with prop-2-en-1-ol in the presence of a palladium catalyst and a base;
wherein $X_3$ is chloro, bromo, or iodo.

In some embodiments, $X_3$ is bromo.

In some embodiments, Heck coupling reaction conditions are utilized, using palladium(0) or palladium(II) catalysts and performed under conditions known in the art (see, e.g., Melpolder and Heck, *J. Org. Chem.* 1976, 41, 265-272, or Littke and Fu, *J. Am. Chem. Soc.* 2001, 123, 6989-7000, which is hereby incorporated in its entirety). In some embodiments, the palladium catalyst is $Pd_2(dba)_3$ (tris(dibenzylideneacetone)dipalladium(0)). In some embodiments, the palladium catalyst is present in an amount of about 0.01 to about 0.1 equivalents, about 0.01 to about 0.05 equivalents, about 0.01 to about 0.02 equivalents, or about 0.015 equivalents. In some embodiments, the reacting further comprises reacting in the presence of a phosphine ligand, or salt thereof. In some embodiments, the phosphine ligand, or salt thereof, is tris(t-butyl)phosphonium tetrafluoroborate. In some embodiments, the ligand is present in an amount of about 0.01 to about 0.05 equivalents, or about 0.03 equivalents.

In some embodiments, the base is an inorganic base. In some embodiments, the base is an organic base. In some embodiments, the base is a tertiary amine, including but not limited to, N-methyl-N-cyclohexylcyclohexylamine. In some embodiments, the base is an alkali metal carbonate. In some embodiments, the base is present in an amount of about 1 to about 5 equivalents, about 1 to about 2 equivalents, about 1 to about 1.5 equivalents, or about 1.2 equivalents.

In some embodiments, the reacting of the compound of Formula IIc with prop-2-en-1-ol is carried out at a temperature of from about 40° C. to about 80° C., from about 50° C. to about 70° C., or from about 50° C. to about 55° C. In some embodiments, the reacting is carried out in a solvent, including, but not limited to dioxane. In some embodiments, prop-2-en-1-ol is present in an amount of about 1 to about 3 equivalents, or about 2 equivalents.

In some embodiments, the process further comprises preparing the compound of Formula IIa by a process comprising reacting a compound of Formula IId:

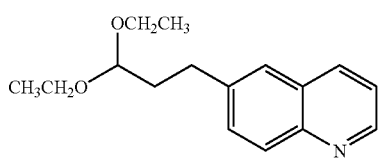

with an acid of formula HX';

wherein X' is chloro, bromo, or iodo.

In some embodiments, X' is chloro.

In some embodiments, the reacting of the compound of Formula IId with the acid is carried out at a temperature of from about 0° C. to about 20° C., from about 0° C. to about 10° C., or from about 0° C. to about 5° C. In some embodiments, the reacting is carried out in a solvent, including, but not limited to, ethyl acetate.

In some embodiments, the process further comprises preparing a compound of Formula IId by a process comprising reducing a compound of Formula IIe:

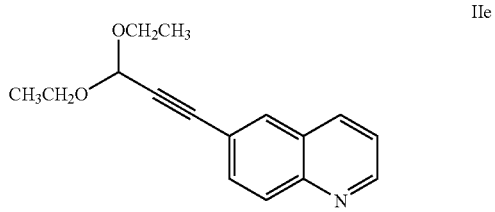

with hydrogen gas in the presence of a hydrogenation catalyst.

In some embodiments, the hydrogenation catalyst is palladium-on-carbon. In some embodiments, the hydrogen gas is at a pressure of about 1 atmosphere. In some embodiments, In some embodiments, the reacting of the compound of Formula IIe with hydrogen gas is carried out at about room temperature.

In some embodiments, the process further comprises preparing a compound of Formula IIe by a process comprising reacting a compound of Formula IIc with a compound of Formula IIf (Sonogashira coupling using, e.g., the method of Ziesel or Kelly, Suffert and Ziesel, *Tetrahedron Lett.* 1991, 32, 757; Kelly, Lee, and Mears, *J. Org. Chem.* 1997, 62, 2774.):

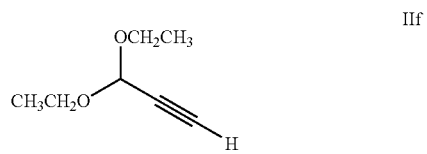

in the presence of a coupling catalyst and a base.

In some embodiments, the coupling catalyst is a palladium catalyst, including, but not limited to, palladium acetate. In some embodiments, the catalyst is a mixture of palladium acetate and CuI. In some embodiments, the base is an inorganic base. In some embodiments, the base is an organic base. In some embodiments, the base is a tertiary amine, including but not limited to, triethylamine. In some embodiments, the base is an alkali metal carbonate. In some embodiments, the base is present in an amount of about 2 to about 10 equivalents, about 4 to about 9 equivalents, about 6 to about 8 equivalents, or about 7.2 equivalents.

In some embodiments, the reacting further comprises reacting in the presence of a phosphine ligand, or salt thereof, including, but not limited to, triphenylphosphine. In some embodiments, the palladium acetate is present in an amount of about 0.01 to about 0.05 equivalents, or about 0.03 equivalents. In some embodiments, the copper(I) iodide is present in an amount of about 0.005 to about 0.2 equivalents, or about 0.01 equivalents. In some embodiments, the phosphine ligand, or salt thereof, is present in an amount of about 0.005 to about 0.2 equivalents, or about 0.012 equivalents.

In some embodiments, the reacting is carried out at a temperature of from about 70° C. to about 100° C., from about 80° C. to about 100° C., or about 90° C. In some embodiments, the reacting is carried out in a solvent, including, but not limited to dimethylformamide. In some embodiments, the compound of Formula IIf is present in an amount of about 1 to about 3 equivalents, or about 2 equivalents.

In some embodiments, the process further comprises preparing a compound of Formula IId:

IId

[Structure: quinoline substituted at 6-position with -CH2CH2CH(OCH2CH3)(OCH2CH3) - a diethyl acetal-containing chain]

by a process comprising reacting a compound of Formula IIg:

IIg

[Structure: CH2=CH-CH(OCH2CH3)(OCH2CH3)]

with 9-borabicyclo[3.3.1]nonane (9-BBN), followed by reacting with a compound of Formula IIc:

IIc

[Structure: 6-X3-quinoline]

in the presence of a coupling catalyst to form the compound of Formula IId, wherein $X_3$ is chloro, bromo, or iodo.

In some embodiments, $X_3$ is chloro.

In some embodiments, the 9-BBN is added directly. In some embodiments, the 9-BBN is generated in situ (Soderquist and Negron, *J. Org. Chem.*, 1987, 52, 3441-3442). In some embodiments, the compound of Formula IIg is present in an amount of about 1 to about 3 equivalents, or about 1.5 to about 2.5 equivalents, or about 1.75 equivalents.

In some embodiments, coupling reaction conditions are utilized, using palladium(0) or palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is palladium(II) acetate. In some embodiments, the palladium catalyst is present in an amount of about of about 0.01 to about 0.1 equivalents, about 0.01 to about 0.1 equivalents, about 0.02 to about 0.07 equivalents, or about 0.05 equivalents.

In some embodiments, the reacting further comprises reacting in the presence of a phosphine ligand, or salt thereof. In some embodiments, the phosphine ligand is tricyclohexylphosphine. In some embodiments, the phosphine ligand, or salt thereof is present in an amount of about 0.05 to about 0.2 equivalents, or about 0.1 equivalents.

In some embodiments, the second step is carried out in a solvent, including, but not limited to, tetrahydrofuran, water, or mixtures thereof.

In some embodiments, the second step is carried out at the reflux temperature.

In some embodiments, the process further comprises preparing the compound of Formula III by a process comprising reacting a compound of Formula IIIa:

IIIa

[Structure: 1,2,4-triazine with X4 at 5-position and NH2 at 3-position]

with a compound of Formula IIIb:

IIIb

[Structure: 4-cyano-3-fluorophenyl boronic ester with OR_a groups]

in the presence of a palladium catalyst and a base; wherein:
$X_4$ is chloro, bromo or iodo; and
each $R_a$ is, independently, $C_{1-6}$ alkyl; or
each $R_a$, along with the two oxygen atoms and boron atom form a 5- or 6-membered heterocyclic ring; wherein the heterocyclic ring is optionally substituted with 1, 2, 3, or 4 independently selected $C_{1-4}$ alkyl groups.

In some embodiments, $X_4$ is bromo.

In some embodiments, the compound of Formula IIIb has formula IIIb-1:

IIIb-1

[Structure: 4-cyano-3-fluorophenyl pinacol boronate]

In some embodiments, $X_4$ is bromo.

In some embodiments, Suzuki coupling reaction conditions are utilized, using palladium(0) or palladium(II) catalysts and performed under conditions known in the art (see, e.g., Miyaura and Suzuki, *Chem. Rev.* 1995, 95, 2457-2483, which is hereby incorporated in its entirety). In some embodiments, the palladium catalyst is 1,1'-bis(diphenylphosphino) ferrocene dichloropalladium(II) (Pd(dppf)$_2$Cl$_2$). In some embodiments, the palladium catalyst is present in an amount of about of about 0.1 to about 0.5 equivalents, about 0.2 to about 0.4 equivalents, or about 0.3 equivalents.

In some embodiments, the base is an inorganic base. In some embodiments, the base is an organic base. In some embodiments, the base is a tertiary amine. In some embodiments, the base is an alkali metal carbonate (e.g., potassium carbonate or sodium carbonate).

In some embodiments, the reacting is carried out at a temperature of from about 60° C. to about 100° C., from about 70° C. to about 90° C., from about 80° C. to about 90° C., or about 86° C. In some embodiments, the reacting is carried out in a solvent, including, but not limited to, dioxane. In some embodiments, the compound of Formula IIIb or IIIb-1 is present in an amount of about 1 to about 2 equivalents, or about 1.3 equivalents.

In some embodiments, the process further comprises preparing the compound of Formula IIIa by reacting 1,2,4-triazine-3-amine with a halogenating agent.

In some embodiments, $X_4$ is bromo; and the halogenating agent is N-bromosuccinimide. In some embodiments, the halogenating agent is present in an amount of about 1 to about 2 equivalents, or about 1 to about 1.1 equivalents.

In some embodiments, the process further comprises preparing 1,2,4-triazine-3-amine by a process comprising reacting glyoxal with aminoguanidine, or salt thereof.

In some embodiments, the process further comprises preparing the compound of Formula IIIb-1 by a process comprising:

a) reacting a compound of Formula IIIc:

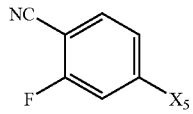

a reagent of formula $R_1MgY$, followed by reacting with a compound of formula $B(OR_2)_3$ to form a compound of Formula IIId:

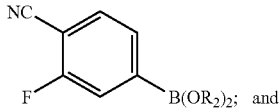

b) after the reacting in step a), reacting the compound of Formula IIId with an acid, followed by reacting with pinacol to form the compound of Formula IIIb-1; wherein:

$R_1$ is $C_{1-6}$ alkyl;

each $R_2$ is, independently, $C_{1-6}$ alkyl; and $X_5$ is chloro, bromo, or iodo.

In some embodiments, $X_5$ is bromo. In some embodiments, $R_1$ is isopropyl. In some embodiments, $R_2$ is methyl. In some embodiments, the $B(OR_2)_3$ is present in an amount of about 1 to about 2 equivalents, or about 1.4 equivalents. In some embodiments, step a) is carried out a temperature of from about 0 to about 25° C., or from about 7 to about 16° C.

In some embodiments, the pinacol is present in an amount of about 1 to about 3 equivalents, or about 2 equivalents. In some embodiments, step b) is carried out at a temperature of about room temperature to about 50° C. In some embodiments, step b) is carried out in a solvent, including but not limited to, cyclohexane.

The present invention further provides a process of preparing a compound of Formula I:

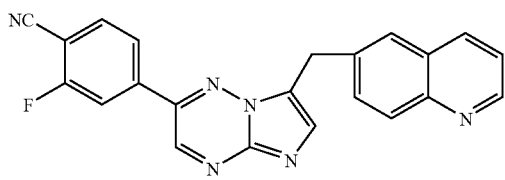

or salt thereof; comprising:

a) reacting a compound of Formula II:

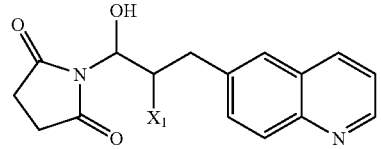

with a compound of Formula VII:

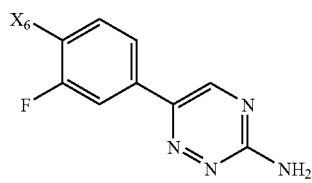

to form a compound of Formula VIa:

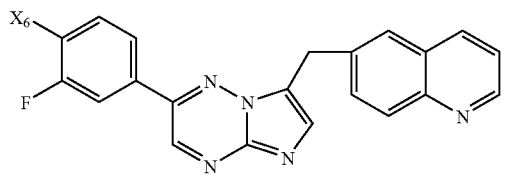

and b) reacting the compound the compound of Formula VIa with $Zn(CN)_2$ and Zn in the presence of a catalyst to form the compound of Formula I, or salt thereof;

wherein $X_6$ is chloro, bromo, or iodo.

In some embodiments, the compound of Formula I is converted to a compound of Formula V by the process steps described supra.

In some embodiments, $X_6$ is bromo.

In some embodiments, the compound of Formula II and the compound of Formula VII are present in about 1.1 to about 0.67 equivalents, respectively. In some embodiments, step a) is carried out in a solvent, including, but not limited to, 1-butanol. In some embodiments, step a) is carried out at a temperature of about 100° C. to about 120° C., or about 110° C.

In some embodiments, the catalyst is a palladium(II) or palladium(0) catalyst. In some embodiments, the catalyst further comprises a phosphine ligand. In some embodiments, the catalyst is 1,1'-bis(diphenylphosphino)ferrocene dichloropalladium(II) ($Pd(dppf)_2Cl_2$). In some embodiments, the Zn is present in an amount of about 0.1 to about 0.3 equivalents, or about 0.2 equivalents. In some embodiments, the $Zn(CN)_2$ is present in an amount of about 0.5 to about 1 equivalents, or about 0.6 equivalents. In some embodiments, the catalyst is present in an amount of about 0.03 to about 0.1 equivalent, or about 0.06 equivalent. In some embodiments, step b) is carried out in a solvent, including, but not limited to, dimethylacetamide, water, or a mixture thereof. In some embodiments, step b) is carried out at a temperature of about 100° C. to about 120° C., or about 110° C.

In some embodiments, the process further comprises preparing the compound of Formula VII by a process comprising reacting a compound of Formula VIII:

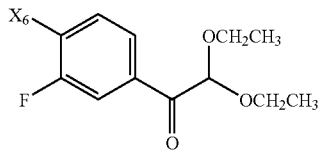

VIII with aminoguanidine, or salt thereof, and a base;
wherein $X_6$ is chloro, bromo, or iodo.

In some embodiments, $X_6$ is bromo.

In some embodiments, the base is an alkali metal hydroxide (e.g., sodium hydroxide or potassium hydroxide). In some embodiments, the base is potassium hydroxide. In some embodiments, the aminoguanidine, or salt thereof, is present in an amount of about 1 to about 3 equivalents, or about 2 equivalents. In some embodiments, the base is present in an amount of about 3 to about 5 equivalents, or about 4 equivalents. In some embodiments, the reacting is carried out at a temperature of from about 60° C. to about 80° C., or about 75° C.

In some embodiments, the process further comprises preparing forming the compound of Formula VIII by a process comprising reacting a compound of Formula IX:

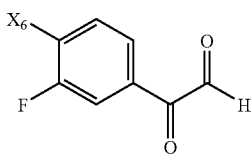

IX with triethyl orthoformate to form a compound of Formula VIII in the presence of an acid;
wherein $X_6$ is chloro, bromo, or iodo.

In some embodiments, $X_6$ is bromo.

In some embodiments, the acid is p-toluenesulfonic acid. In some embodiments, the reacting is carried out at a temperature of from about 100° C. to about 120° C., or about 110° C. In some embodiments, the triethyl orthoformate is present in an amount of about 1 to about 4 equivalents, about 2 to about 3 equivalents, or about 2.5 equivalents. In some embodiments, the acid is present in an amount of about 0.1 to about 1 equivalents, about 0.2 to about 0.6 equivalents, or about 0.4 equivalents.

In some embodiments, the process further comprises preparing the compound of Formula IX by a process comprising reacting a compound of Formula X:

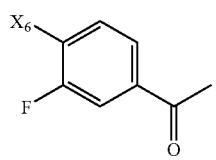

X with a strong acid to form the compound of Formula IX;
wherein $X_6$ is chloro, bromo, or iodo.

In some embodiments, $X_6$ is bromo. In some embodiments, the acid has formula HX', wherein X' is chloro, bromo or iodo. In some embodiments, X' is bromo. In some embodiments, the reacting is carried out in a solvent, including, but not limited to, dimethylsulfoxide. In some embodiments, the acid is HBr combined with DMSO as described in Floyd, Du, Fabio, Jacob, and Johnson *J. Org. Chem.*, 1985, 50, 5022-5027. In some embodiments, the addition of the strong acid is carried out at about room temperature and then the reaction mixture is heated to a temperature of from about 50° C. to about 70° C., or about 60° C.

In some embodiments, the process further comprises preparing the compound of Formula X by a process comprising reacting the compound of Formula XI:

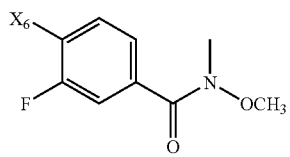

XI with $CH_3MgBr$ to form a compound of Formula X;
wherein $X_6$ is chloro, bromo, or iodo.

In some embodiments, the $CH_3MgBr$ is present in an amount of about 1 to about 3 equivalents, or about 1.7 equivalents. In some embodiments, the reacting is carried out at a temperature of about 0° C. to about 15° C., about 0° C. to about 5° C., or at about 0° C.

In some embodiments, the process further comprises preparing the compound of Formula XI by a process comprising reacting the compound of Formula XII:

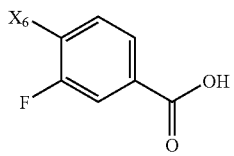

XII with oxalyl chloride or thionyl chloride, followed by treating with dimethyl hydroxylamine, or salt thereof to form a compound of Formula XI.

In some embodiments, the reacting is carried out with oxalyl chloride. In some embodiments, the oxalyl chloride is present in an amount of about 1 to about 2 equivalents, or about 1.4 to about 1.5 equivalents. In some embodiments, the reacting is carried out in a solvent, including but not limited to, methylene chloride. In some embodiments, the reacting is carried out at a temperature of about room temperature.

In some embodiments, any of the intermediates described in the embodiments herein may be present as the free base. In some embodiments, any of the intermediates described in the embodiments herein may be present as a salt. In some embodiments, the intermediates described herein are the hydrate or solvate form.

In some embodiments, the present invention provides any of the individual process steps or intermediate compounds described supra.

At various places in the present specification, substituents of compounds are disclosed in groups or in ranges. It is specifically intended that the compounds include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substitutent. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 12, 1 to 8, 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, the term "5-membered or 6-member heterocyclic ring" in the context of a moiety of formula —B(OR$_a$)$_2$, refers to a saturated monocyclic ring with 5 or 6 ring members including the two oxygen atoms and the one boron atom, wherein the remaining 2 or 3 ring members are carbon atoms.

As used herein, the term "about" refers to plus or minus 10% of the value.

As used herein, the expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, or spectrophotometry (e.g., UV-visible); or by chromatography such as high performance liquid chromatograpy (HPLC) or thin layer chromatography (TLC).

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The compounds can also include salt forms of the compounds and intermediates described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents.

The compounds and intermediates also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used, to isolate the desired products.

Pharmaceutical Formulations and Dosage Forms

When employed as pharmaceuticals, the salts of the invention can be administered in the form of pharmaceutical compositions, such as a salt of the invention combined with at least one pharmaceutically acceptable carrier. These compositions can be prepared in a manner well known in the pharmaceutical arts, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, a salt of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The salt of the invention may be milled using known milling procedures such as wet milling to obtain a particle size appropriate for tablet formation and for other formulation types. Finely divided (nanoparticulate) preparations of the salt of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the salt of the present invention can vary according to, for example, the particular use for which the treatment is made, the manner of administration of the compound, the health and condition of the patient, and the judgment of the prescribing physician. The proportion or concentration of the salt of the invention in a pharmaceutical composition can vary depending upon a number of factors including dosage, chemical characteristics (e.g., hydrophobicity), and the route of administration. For example, the salt of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The salts of the invention can also be formulated in combination with one or more additional active ingredients which can include any pharmaceutical agent such as anti-viral agents, vaccines, antibodies, immune enhancers, immune suppressants, anti-inflammatory agents and the like.

Labeled Compounds and Assay Methods

Another aspect of the present invention relates to a fluorescent dye, spin label, heavy metal or radio-labeled salt of the invention that would be useful not only in imaging but also in assays, both in vitro and in vivo, for localizing and quantitating the protein kinase target in tissue samples, including human, and for identifying kinase ligands by inhibition binding of a labeled compound. Accordingly, the present invention includes kinase enzyme assays that contain the labeled salt.

The present invention further includes isotopically-labeled compounds of the compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled salt of the invention can be used in a screening assay to identify/evaluate compounds. In general terms, a newly synthesized or identified compound (i.e., test compound) can be evaluated for its ability to reduce binding of the radio-labeled salt of the invention to the enzyme. Accordingly, the ability of a test compound to compete with the radio-labeled salt for binding to the enzyme directly correlates to its binding affinity.

Kits

The present invention also includes pharmaceutical kits useful, for example, in the treatment or prevention of diseases, such as cancer and other diseases referred to herein, which include one or more containers containing a pharmaceutical composition comprising a therapeutically effective amount of the salt of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 2-Fluoro-N-methyl-4-[7-(quinolin-6-ylmethyl)imidazolo[1,2-b][1,2,4]triazin-2-yl]benzamide dihydrochloric acid salt A suspension of 2-fluoro-N-methyl-4-[7-(quinolin-6-ylmethyl)imidazolo[1,2-b][1,2,4]triazin-2-yl]benzamide (421.2 g, 1.021 mol) (see U.S. Ser. No. 11/942,130 for preparation, the disclosure of which is incorporated herein by reference in its entirety) in methanol (MeOH, 6600 mL) was heated to 55° C. before a premixed solution of aqueous concentrated hydrochloric acid (conc. HCl, 37 wt. %, 12 M, 420 mL, 5.10 mol, 5.0 equiv) in isopropyl alcohol (IPA, 1510 mL) was added dropwise at 55° C. The resulting clear solution was stirred at 55° C. for 30 min before methyl tert-butyl ether (MTBE, 6750 mL) was added via an addition funnel over 30 min. The solids were slowly precipitated out after addition of methyl tert-butyl ether. The resulting mixture was stirred at 55° C. for an additional 1 h before being gradually cooled down to room temperature. The mixture was stirred at room temperature overnight. The solids were collected by filtration, washed with methyl tert-butyl ether (MTBE, 3×500 mL), and dried in vacuum oven at 45-55° C. to constant weight. The desired 2-fluoro-N-methyl-4-[7-(quinolin-6-ylmethyl)imidazolo[1,2-b][1,2,4]triazin-2-yl]benzamide dihydrochloride (470.7 g, 495.5 g theoretical, 95% yield) was obtained as an off-white to light yellow crystalline solid. M.p. (decom.) 222° C.; $^1$H NMR (400 MHz, DMSO-d$_6$) δ ppm 9.46 (s, 1H), 9.25 (dd, 1H, J=5.4 Hz, 1.4 Hz), 9.12 (d, 1H, J=8.3 Hz), 8.51 (m, 1H), 8.47 (d, 1H, J=0.9 Hz), 8.34 (d, 1H, J=1.3 Hz), 8.23 (s, 1H), 8.21 (dd, 1H, J=9.0 Hz, 1.8 Hz), 8.09-8.02 (m, 3H), 7.79 (dd, 1H, J=7.5 Hz, 8.3 Hz), 4.77 (s, 2H), 2.78 (s, 3H, J=4.5 Hz); $^{13}$C NMR (100 MHz, DMSO-d$_6$) δ ppm 163.4, 159.4 (d, J=249.9 Hz), 145.8, 145.4, 144.5, 143.8, 140.4, 138.8, 136.8, 135.9, 135.7 (J=8.6 Hz), 131.2 (J=3.1 Hz), 130.7, 128.7, 128.2, 126.2 (J=14.9 Hz), 126.0, 123.1 (J=3 Hz), 122.5, 121.0, 114.9 (J=5.6 Hz), 28.4, 26.3; $^{19}$F NMR (376.3 MHz, DMSO-d$_6$) δ ppm −113.2; C$_{23}$H$_{17}$FN$_6$O (free base, MW 412.42), LCMS (EI) m/e 413.1 (M$^+$+H) and 435.0 (M$^+$+Na).

Example 2

X-Ray Powder Diffraction of the Dihydrochloric Acid Salt

XRPD was carried out using a Rigaku MiniFlex X-ray Powder Diffractometer instrument (X-ray radiation is from copper (Cu) at 1.054056 Å with Kβ filter, Start Angle—3; Stop Angle—45; Sampling—0.02; Scan speed—2). The sample powder was dispersed on a zero-background sample holder. The XRPD pattern of the dihydrochloric acid salt prepared by the process of Example 1 is provided in FIG. 1. Two-theta peak values are provided in Table 1 below.

TABLE 1

| 2-Theta | Height | H % |
|---|---|---|
| 3.8 | 58 | 4 |
| 6.0 | 57 | 3.9 |
| 7.8 | 403 | 27.7 |
| 9.1 | 86 | 5.9 |
| 12.0 | 584 | 40.1 |
| 12.6 | 371 | 25.5 |
| 14.3 | 202 | 13.9 |
| 14.9 | 306 | 21 |
| 15.9 | 346 | 23.8 |
| 16.3 | 277 | 19 |
| 17.4 | 247 | 17 |
| 18.2 | 1367 | 93.9 |
| 20.0 | 283 | 19.5 |
| 20.5 | 212 | 14.6 |
| 21.4 | 240 | 16.5 |
| 21.8 | 60 | 4.1 |
| 22.4 | 314 | 21.6 |
| 23.3 | 281 | 19.3 |
| 23.9 | 176 | 12.1 |
| 24.7 | 1362 | 93.6 |
| 25.4 | 81 | 5.6 |
| 26.0 | 1456 | 100 |
| 27.1 | 226 | 15.5 |
| 27.4 | 138 | 9.5 |
| 28.0 | 142 | 9.8 |
| 29.3 | 962 | 66.1 |
| 30.5 | 165 | 11.3 |
| 31.0 | 502 | 34.5 |

TABLE 1-continued

| 2-Theta | Height | H % |
|---------|--------|-----|
| 31.9 | 76 | 5.3 |
| 33.0 | 485 | 33.3 |
| 33.4 | 285 | 19.6 |
| 34.5 | 166 | 11.4 |
| 35.4 | 78 | 5.4 |
| 36.2 | 381 | 26.1 |
| 37.2 | 449 | 30.9 |
| 38.4 | 190 | 13.1 |
| 39.8 | 82 | 5.7 |
| 40.5 | 79 | 5.4 |
| 42.4 | 99 | 6.8 |
| 43.7 | 107 | 7.4 |

Example 3

Differential Scanning Calorimetry of the Dihydrochloric Acid Salt

Figure 2:
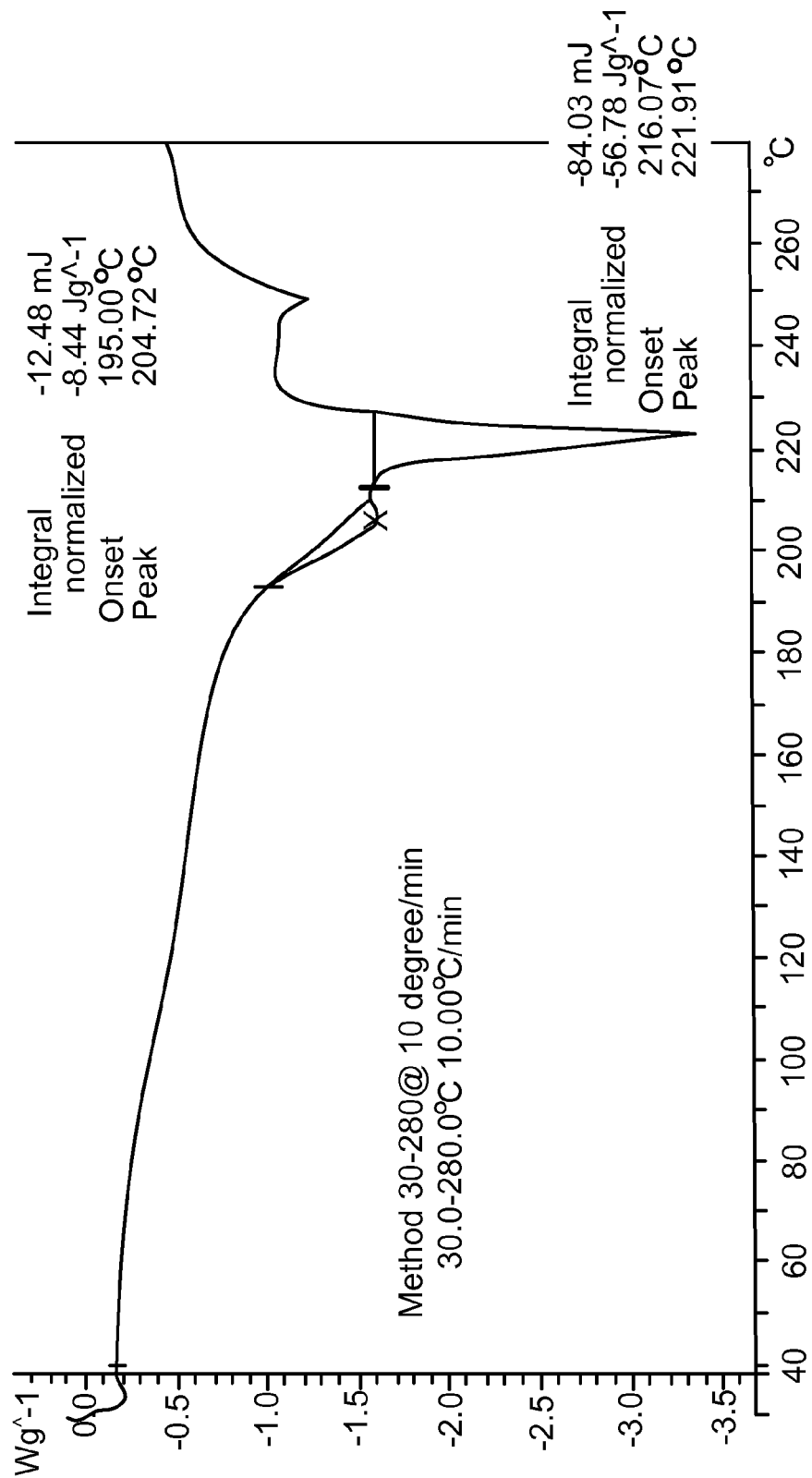
FIG. 2 shows a differential scanning calorimetry (DSC) trace characteristic of a dihydrochloric acid salt of the invention prepared according to the process of Example 1.

The dihydrochloric acid salt prepared by the process of Example 1 is characterized by the DSC trace shown in FIG. 2. The DSC thermogram revealed an endothermic event with peak onset at 216.1° C. and a peak at 221.91° C. The experiments were carried out on a Mettler Toledo Differential Scanning Calorimetry (DSC) 822 instrument, with an aluminum sample pan (40 µL), initial temperature of 30° C. to a final temperature of 280° C. using a heating rate of 10° C./min.

Example 4

Thermogravimetric Analysis of the Dihydrochloric Acid Salt

Figure 3:
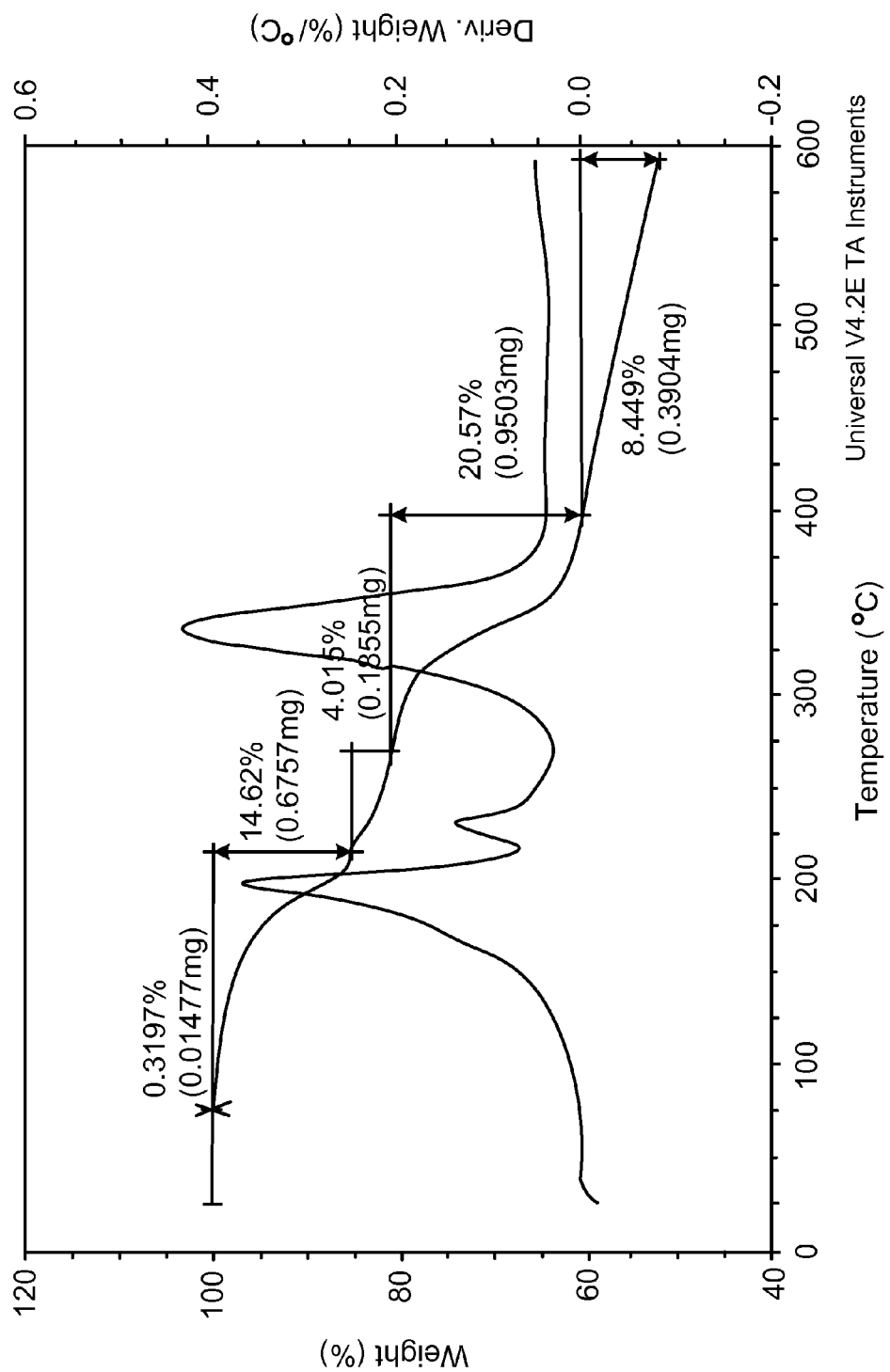
FIG. 3 shows a thermogravimetric analysis (TGA) thermogram characteristic of a dihydrochloric acid salt of the invention prepared according to the process of Example 1.

The dihydrochloric acid salt prepared by the process of Example 1 is characterized by the TGA shown in FIG. 3. The TGA showed significant weight loss starting at 150° C. when the sample was heated from 20° C. to 600° C. at a heating rate of 20° C./min. This was followed by an exothermic event with a peak at 221.9° C. which was believed to be the melting peak. The experiments were carried out on TA Instrument Q500.

Example 5

Preparation of 2-Fluoro-N-methyl-4-[7-(quinolin-6-ylmethyl)imidazolo[1,2-b][1,2,4]triazin-2-yl]benzamide dibenzenesulfonic acid salt A suspension of 2-fluoro-N-methyl-4-[7-(quinolin-6-ylmethyl)imidazolo[1,2-b][1,2,4]triazin-2-yl]benzamide (500 mg, 1.212 mmol) in methanol (MeOH, 12 mL) was heated to 55° C. before a premixed solution of benzenesulfonic acid (578 mg, 3.65 mmol, 3.01 equiv) in isopropyl alcohol (IPA, 3.66 mL) was added dropwise at 55° C. The resulting clear solution was stirred at 55° C. for 30 min before methyl tert-butyl ether (MTBE, 12 mL) was added dropwise via an additional funnel. The solids were slowly precipitated out after addition of methyl tert-butyl ether. The resulting mixture was stirred at 55° C. for one an additional hour before being gradually cooled down to room temperature. The mixture was stirred at room temperature overnight. The solids were collected by filtration, washed with methyl tert-butyl ether (MTBE, 2×10 mL), and dried in vacuum oven at 45-55° C. to constant weight. The desired dibenzenesulfonic acid product (848 mg, 883.3 mg theoretical, 96% yield) was obtained as off-white crystalline solids. M.p. (decom.) 270.5° C.; $^1$H NMR (400 MHz, DMSO-$d_6$) δ ppm 9.51 (s, 1H), 9.30 (dd, 1H, J=5.4 Hz, 1.4 Hz), 9.13 (d, 1H, J=8.3 Hz), 8.45 (m, 1H), 8.36 (d, 1H, J=0.9 Hz), 8.30 (s, 1H), 8.21 (dd, 2H, J=9.0 Hz, 1.8 Hz), 8.10-8.04 (m, 3H), 7.80 (dd, 1H, J=7.5 Hz, 8.3 Hz), 7.62-7.56 (m, 4H), 7.33-7.27 (m, 6H), 4.79 (s, 2H), 2.78 (d, 3H, J=4.5 Hz); $^{19}$F NMR (376.3 MHz, DMSO-$d_6$) δ ppm −113.2; $C_{23}H_{17}FN_6O$ (free base, MW 412.42), LCMS (EI) m/e 413.0 (M$^+$+H) and 435.0 (M$^-$+Na).

Example 6

X-Ray Powder Diffraction of the Dibenzenesulfonic Acid Salt

XRPD was carried out using a Rigaku MiniFlex X-ray Powder Diffractometer instrument (X-ray radiation is from copper (Cu) at 1.054056 Å with Kβ filter, Start Angle—3; Stop Angle—45; Sampling—0.02; Scan speed—2). The XRPD pattern of the salt prepared by the process of Example 5 is provided in FIG. 4. Two-theta peak values are provided in Table 2 below.

TABLE 2

| 2-Theta | Height | H % |
|---------|--------|-----|
| 4.9 | 688 | 100 |
| 9.9 | 163 | 23.7 |
| 11.1 | 169 | 24.6 |
| 13.8 | 226 | 32.9 |
| 15.0 | 441 | 64.1 |
| 16.3 | 378 | 54.9 |
| 16.7 | 262 | 38.1 |
| 17.6 | 53 | 7.7 |
| 18.3 | 430 | 62.5 |
| 19.0 | 46 | 6.6 |
| 20.2 | 661 | 96.1 |
| 22.2 | 284 | 41.3 |
| 22.8 | 93 | 13.6 |
| 23.8 | 460 | 66.8 |
| 24.8 | 244 | 35.5 |
| 25.2 | 306 | 44.5 |
| 26.7 | 237 | 34.4 |
| 27.0 | 212 | 30.9 |
| 29.4 | 95 | 13.8 |
| 30.4 | 66 | 9.6 |
| 31.1 | 47 | 6.8 |
| 31.9 | 39 | 5.6 |
| 33.0 | 54 | 7.8 |
| 34.1 | 75 | 10.8 |
| 34.8 | 42 | 6.2 |
| 35.1 | 43 | 6.3 |
| 40.0 | 48 | 7 |
| 40.5 | 58 | 8.4 |
| 42.1 | 35 | 5 |

Example 7

Differential Scanning Calorimetry of the Dibenzenesulfonic Acid Salt

Figure 5:
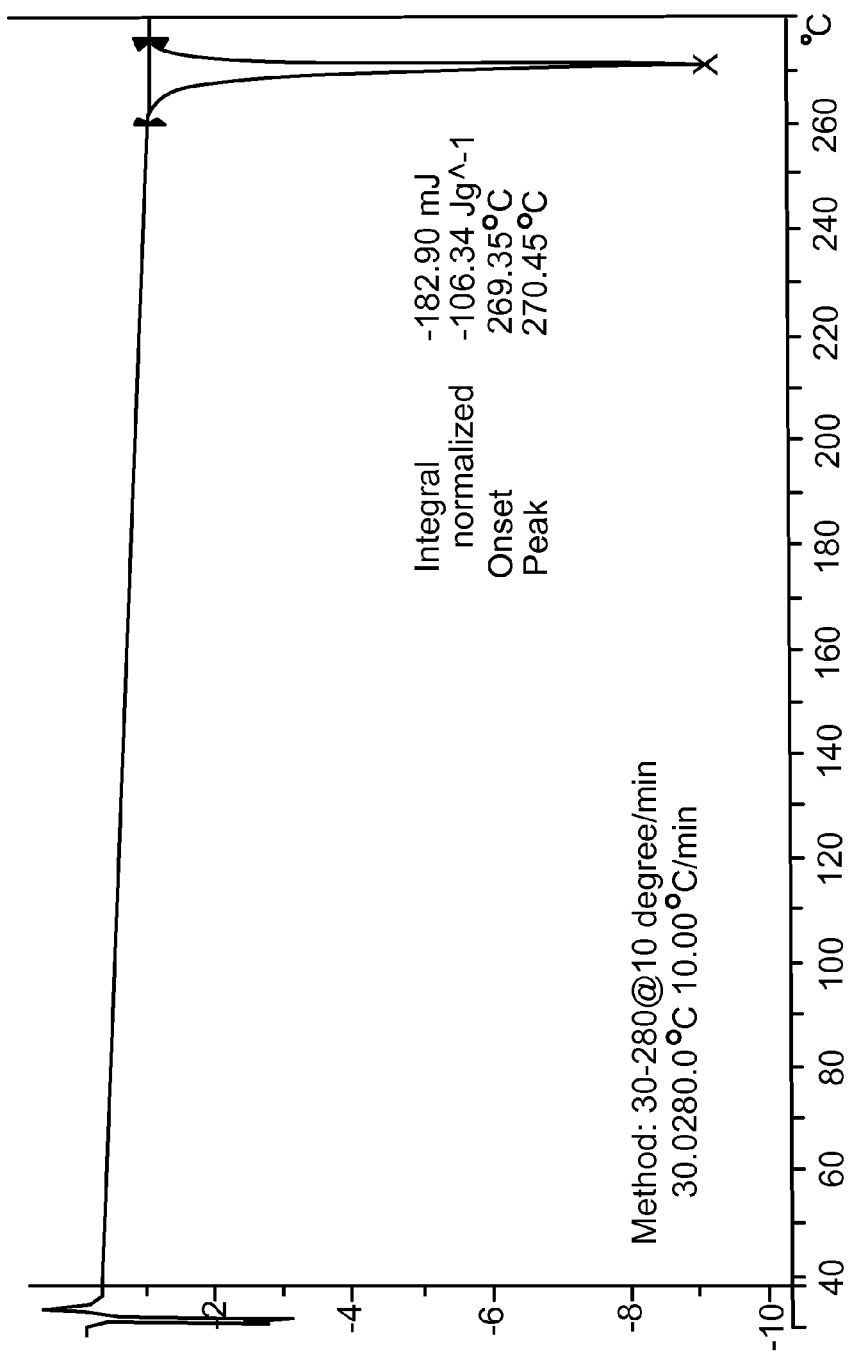
FIG. 5 shows a differential scanning calorimetry (DSC) trace characteristic of a dibenzenesulfonic acid salt of the invention prepared according to the process of Example 5.

The dibenzenesulfonic acid salt prepared by the process of Example 5 is characterized by the DSC trace shown in FIG. 5. The DSC thermogram revealed one endothermic event with an onset at 269.4° C. followed by an exothermic event with a peak at 270.45° C. The experiments were carried out on a Mettler Toledo Differential Scanning Calorimetry (DSC) 822 instrument, initial temperature of 30° C. to a final temperature of 280° C. using a heating rate of 10° C./min.

Example 7A

Physical Characteristics of the Dibenzenesulfonic Acid Salt

The dibenzenesulfonic acid salt is generally an off-white to light yellow powder in a visual inspection against a white background.

Example 7B

Solubility of the Dibenzenesulfonic Acid Salt

The dibenzenesulfonic acid salt is generally obtained as a off-white to light yellow powder in a visual inspection against a white background. The solubility of the dibenzenesulfonic acid salt at 25° C. was found to be approximately 3.9 mg/mL in water; 0.003 mg/mL in pH 7.4 buffer; 0.003 mg/mL in pH 8.0 buffer; and at least 29 mg/mL in 0.1 N aqueous HCl.

The equilibrium solubility was determined by mixing the sample in the selected aqueous solvents (0.1 N HCl, water, pH 7.4 buffer, and pH 8.0 buffer) for at least 12 hours. The sample concentration was then determined by HPLC using a single point calibration.

Example 8

4-Bromo-3-fluoro-N-methoxy-N-methylbenzamide (3)

To a suspension of 4-bromo-3-fluorobenzoic acid (1, 967.9 g, 4.4 mol) in dichloromethane (5.9 L) and DMF (21 mL) was slowly added a solution of oxalyl chloride ((COCl)$_2$, 560 mL, 6.4 mol, 1.45 equiv) in dichloromethane (520 mL) at room temperature. The resulting reaction mixture was stirred at room temperature for 20 h and then cooled to 0° C. by ice-water bath. N,O-dimethyl hydroxylamine hydrochloride (826 g, 8.4 mol, 1.9 equiv) was added followed by slow addition of triethylamine (TEA, 2.5 L, 17.7 mol, 4.0 equiv) at 0° C. The reaction mixture was then gradually warmed to room temperature and stirred at room temperature overnight. Once the coupling reaction was complete, the reaction mixture was washed with saturated aqueous sodium bicarbonate solution (NaHCO$_3$, 2 L). The aqueous phase was back extracted with dichloromethane (1 L). The combined organic phases were washed with water (1 L), brine (1 L), and concentrated under reduced pressure. The resulting solid residue was dissolved into methyl tert-butyl ether (MTBE, 5 L), washed sequentially with water (5×1 L), brine (1 L), and dried over anhydrous sodium sulfate (Na$_2$SO$_4$). The filtrated solution was concentrated under reduced pressure and the resulting solid was dried in a vacuum oven at 45° C. to afford 4-bromo-3-fluoro-N-methoxy-N-methylbenzamide (3, 1106 g, 1153 g theoretical, 95.9% yield) which was used for the subsequent reaction without further purification. For 3: $^1$H NMR (400 MHz, DMSO-d$_6$) δ ppm 7.78 (t, 1H, J=7.47 Hz), 7.56 (dd, 1H, J=9.3, 1.6 Hz), 7.18 (d, 1H, J=8.1 Hz), 3.53 (s, 3H), 3.25(s, 3H); C$_9$H$_9$BrFNO$_2$ (MW 262.08), LCMS (EI) m/e 262.0/264.0 (M$^+$+H).

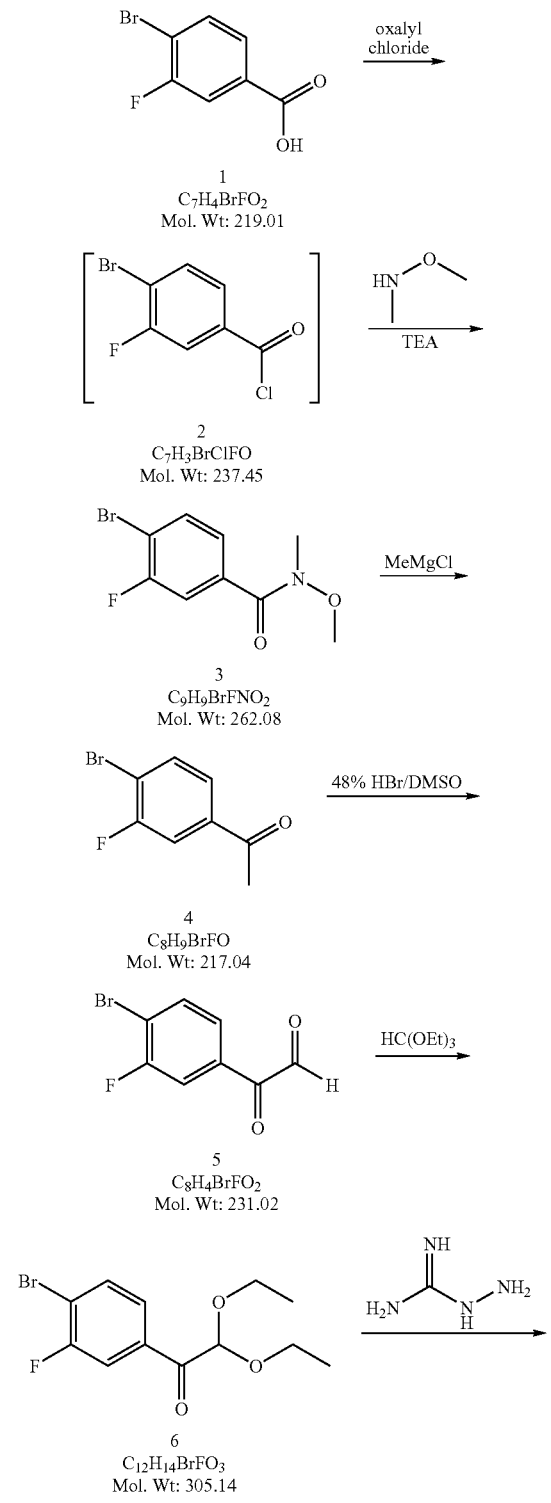

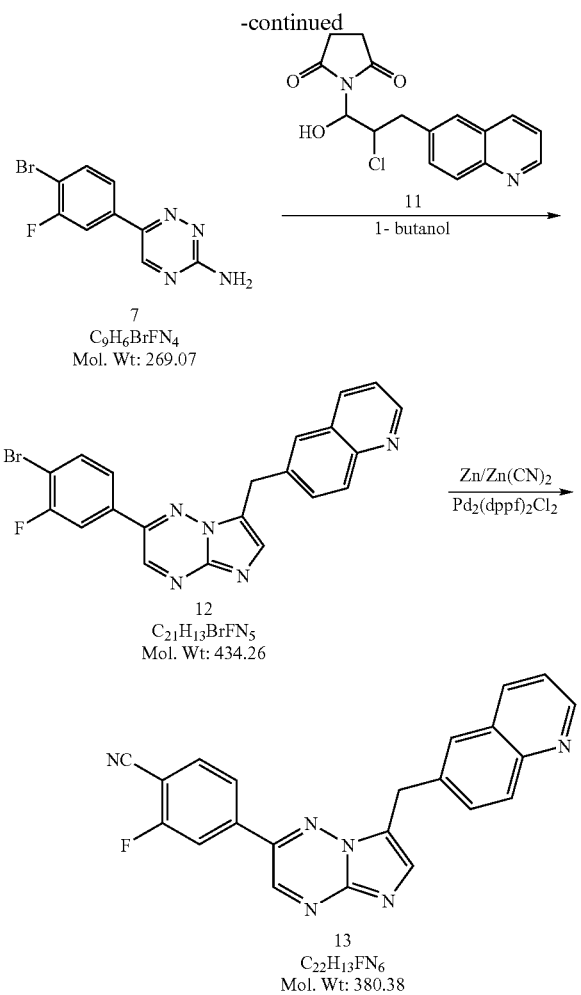

Example 9

1-(4-Bromo-3-fluorophenyl)ethanone (4)

To a solution of crude 4-bromo-3-fluoro-N-methoxy-N-methylbenzamide (3, 1106 g, 4.2 mol) in anhydrous tetrahydrofuran (THF, 11 L) was slowly added a 3.0 M solution of methylmagnesium chloride (MeMgCl, 2.5 L, 7.5 mol, 1.7 equiv) in THF at 0° C. The resulting reaction mixture was stirred at 0° C. for 2 h and then quenched very carefully with saturated aqueous ammonium chloride (NH$_4$Cl, 1.5 L). The resulting solution was concentrated under reduced pressure to remove most of THF. The residue was then diluted with ethyl acetate (EtOAc, 5 L) and the resulting solution was washed with water (2 L). The aqueous phase was extracted with ethyl acetate (EtOAc, 2×2 L). The combined organic phases were washed with water (2 L), brine (2 L) and dried over anhydrous sodium sulfate (Na$_2$SO$_4$). The filtered solution was concentrated under reduced pressure and the resulting solid was dried in a vacuum oven at 45° C. to afford 1-(4-bromo-3-fluorophenyl)ethanone (4, 890.8 g, 911.6 g theoretical, 97.7% yield) as a solid which was used in the subsequent reaction without further purification. For 4: $^1$H NMR (400 MHz, DMSO-d$_6$) δ ppm 7.89-7.84 (m, 2H), 7.71 (dd, 1H, J=8.30, 1.87 Hz), 2.57 (s, 3H).

Example 10

2-(4-Bromo-3-fluorophenyl)-2-oxoacetaldehyde (5)

To a solution of 1-(4-bromo-3-fluorophenyl)ethanone (4, 890.8 g, 4.1 mol) in DMSO (4 L) was slowly added a solution of 48% aqueous hydrogen bromide (HBr, 1420 ML, 12.5 mol, 3.0 equiv). The reaction temperature was gradually increased from 20° C. to 50° C. during the course of the addition. The reaction mixture was subsequently heated to 60° C. and stirred at 60° C. overnight. The resulting dimethyl sulfide was removed by distillation and the residue was poured into ice water (28 L). The resulting yellow precipitate was collected by filtration (save the filtrate) and washed with water (5 L). The yellow solid was dissolved in ethyl acetate (EtOAc, 5 L), washed with brine (1 L) and dried over anhydrous sodium sulfate (Na$_2$SO$_4$). The solution was then concentrated under the reduced pressure and the resulting solid was dried in a vacuum oven at 45° C. to give the desired product, 2-(4-bromo-3-fluorophenyl)-2-oxoacetaldehyde, as its hydrate (hydrate of 5, 730.6 g, 1020.9 g theoretical, 71.6% yield). The aqueous phase (filtrate) was extracted with ethyl acetate (3×5 L) and the combined organic phase was washed with water (2×2 L), brine (2 L) and dried over anhydrous sodium sulfate (Na$_2$SO$_4$). The solution was concentrated under reduced pressure and the resulting solid was dried in a vacuum oven at 45° C. to give the second crop of 2-(4-bromo-3-fluorophenyl)-2-oxoacetaldehyde hydrate (hydrate of 5, 289.4 g, 1020.9 g theoretical, 28.3% yield; total 1020 g, 1020.9 g theoretical, 99.9% yield) which was used in the subsequent reaction without further purification. For hydrate of 5: $^1$H NMR (400 MHz, DMSO-d$_6$) δ ppm 8.00-7.70 (m, 3H), 6.69 (br s, 2H), 5.59 (s, 1H).

Example 11

1-(4-Bromo-3-fluorophenyl)-2,2-diethoxyethanone (6)

A 22 L flask was charged with the hydrate of (4-bromo-3-fluorophenyl)-2-oxoacetaldehyde (5, 1020 g, 4.41 mol), toluene (7.5 L), triethyl orthoformate (1633 g, 1.8 L, 11.04 mol, 2.5 equiv), para-toluene sulfonic acid (33.5 g, 0.176 mol, 0.4 equiv) at room temperature, and the resulting reaction mixture was heated to 110° C. and stirred at 110° C. for 6 h. When HPLC showed that the reaction was complete, the reaction mixture was cooled down to room temperature before being poured into a 50 L separation funnel along with ethyl acetate (7.5 L) and the saturated aqueous sodium bicarbonate solution (NaHCO$_3$, 3 L). The mixture was stirred and the layers were separated. The aqueous layer was extracted with ethyl acetate (2 L). The combined organic layers were washed with brine (4 L), dried with sodium sulfate (Na$_2$SO$_4$), and concentrated under the reduced pressure to afford crude 1-(4-bromo-3-fluorophenyl)-2,2-diethoxyethanone (6, 1240 g, 1345.7 g theoretical, 92.1% yield) which was used in the subsequent reaction without further purification. For 6: $^1$H NMR (400 MHz, DMSO-d$_6$) δ ppm 7.94-7.94 (m, 2H), 7.78 (dd, 1H, J=8.51, 2.08 Hz), 5.40 (s, 1H), 3.77-3.60 (m, 4H), 1.16-1.14 (m, 6H).

Example 12

6-(4-Bromo-3-fluorophenyl)-1,2,4-triazin-3-amine (7)

A 22 L flask was charged with 1-(4-bromo-3-fluorophenyl)-2,2-diethoxyethanone (6, 1240 g, 4.07 mol), ethanol (11

L), water (1.4 L), potassium hydroxide (KOH, 910 g, 16.3 mol, 4.0 equiv), and aminoguanidine bicarbonate (1105 g, 8.13 mol, 2.0 equiv) at room temperature. The resulting reaction mixture was then heated to 75° C. for 14 h. When HPLC showed the condensation reaction was deemed complete, the reaction mixture was cooled down to room temperature before being filtered. The filtrate was then concentrated under the reduced pressure to remove the most of the solvents. The residual aqueous solution was extracted with ethyl acetate (EtOAc, 3×6 L). The organic layers were combined and concentrated under the reduced pressure to give a dark brown solid. This solid was dissolved in ethanol (4 L) and the resulting solution was treated with a solution of 0.2 M aqueous hydrochloric acid solution (4 L). The resulting slurry was subsequently heated to 50° C. for 6 h before being allowed to cool down to room temperature. A solution of saturated aqueous sodium bicarbonate solution ($NaHCO_3$, 2 L) was slowly added to the slurry and the resulting mixture was then concentrated under the reduced pressure to remove most of the solvents. The aqueous residue was then treated with ethyl acetate (20 L) to dissolve the solids. The two layers were separated and the aqueous layer was extracted with ethyl acetate (2×2 L). The combined organic layers were concentrated under the reduced pressure. The dark brown solids were treated with methyl tert-butyl ether (MTBE, 4 L) and the resulting slurry was heated to 30° C. and stirred at 30° C. for 30 min. The mixture was filtered and the solids (green to orange in color) were collected (save the filtrate) and washed with methyl tert-butyl ether (MTBE, 2 L) to give the first crop of the crude desired product (7). The filtrate was evaporated under the reduced pressure, and the resulting dark brown solids were treated with methyl tert-butyl ether (MTBE, 2 L). The resulting slurry was heated to 30° C. and stirred at 30° C. for 30 min. The mixture was filtered to give the second crop of the crude desired product (7) which was washed with MTBE (1 L). The combined solids were dried in vacuum at 40-45° C. to afford 6-(4-bromo-3-fluorophenyl)-1,2,4-triazin-3-amine (7, 585 g, 1095.1 g theoretical, 53.4% yield) which was used in the subsequent reaction without further purification. For 7: $^1H$ NMR (400 MHz, DMSO-$d_6$) δ ppm 8.86 (s, 1H), 7.97 (d, 1H, J=10.79 Hz), 7.81 (m, 2H), 7.52 (br s, 2H); $C_9H_6BrFN_4$ (MW 269.07), LCMS (EI) m/e 269.0/271.1 ($M^{30}$ +H).

Example 13

6-((2-(4-Bromo-3-fluorophenyl)imidazo[1,2-b][1,2,4]triazin-7-yl)methyl)quinoline (12)

1-(2-Chloro-1-hydroxy-3-(quinolin-6-yl)propyl)pyrrolidine-2,5-dione (11, 228 g, 0.74 mol, 1.1 equiv) and 6-(4-bromo-3-fluorophenyl)-1,2,4-triazin-3-amine (7, 181 g, 0.673 mol) were suspended in 1-butanol (1800 mL) and the resulting suspension was heated to 110° C. and stirred at 110° C. for 18 h (the reaction mixture becomes homogeneous at this point). The reaction mixture was then gradually cooled down to room temperature before being further cooled down to 10° C. in an ice bath. The resulting yellow solid was collected by filtration (save the 1-butanol filtrates), washed with cold 1-butanol (3×100 mL) and dried by suction. This solid was then suspended in the saturated aqueous sodium bicarbonate solution ($NaHCO_3$, 500 mL) and the resulting suspension was stirred at room temperature for 1 h to neutralize the corresponding hydrochloride salt. The free base was then filtered, washed with water (500 mL) and dried in a vacuum oven at 45° C. for 18 h to afford the first crop of the crude 6-((2-(4-bromo-3-fluorophenyl)imidazo[1,2-b][1,2,4]triazin-7-yl)methyl)quinoline (12, 125.1 g, 292.3 g theoretical, 42.8% yield). The 1-butanol filtrates were then concentrated under the reduced pressure and the resulting solids were dissolved in dichloromethane ($CH_2Cl_2$, 2 L). The solution was wash with the saturated aqueous sodium bicarbonate solution ($NaHCO_3$, 1 L), dried over sodium sulfates ($Na_2SO_4$), and concentrated under the reduced pressure. The residue was then purified by flash column chromatography ($SiO_2$, 0-10% MeOH—$CH_2Cl_2$ gradient elution) to afford the second crop of 6-((2-(4-bromo-3-fluorophenyl)imidazo[1,2-b][1,2,4]triazin-7-yl)methyl)-quinoline (12, 19.7 g, 292.3 g theoretical, 6.7% yield; total 144.8 g, 292.3 g theoretical, 49.5% yield) as yellow solids. For 12: $^1H$ NMR (400 MHz, DMSO-$d_6$) δ ppm 9.23 (s, 1H), 9.11 (dd, 1H, J=4.98, 1.55 Hz), 8.85 (d, 1H, J=8.09 Hz), 8.25-8.18 (m, 2H), 8.12-8.00 (m, 3H), 7.93-7.86 (m, 3H), 4.70 (s, 2H); $C_{21}H_{13}BrFN_5$ (MW 434.26), LCMS (EI) m/e 434.00/435.95 ($M^+$+H).

Example 14

2-Fluoro-4-(7-(quinolin-6-ylmethyl)imidazo[1,2-b][1,2,4]triazin-2-yl)benzonitrile (13)

6-((2-(4-Bromo-3-fluorophenyl)imidazo[1,2-b][1,2,4]triazin-7-yl)methyl)quinoline (12, 200 g, 0.461 mol), zinc cyanide ($ZnCN_2$, 32.7 g, 0.277 mol, 0.6 equiv), zinc powder (Zn, 6.0 g, 0.093 mol, 0.2 equiv) and Pd(dppf)$_2Cl_2$ (22.6 g 0.028 mol, 0.06 equiv) were suspended in premixed solution of N,N-dimethyl acetamide (DMAC, 2000 mL) and water ($H_2O$, 40 mL). The resulting suspension was then degassed with a stream of nitrogen for 20 min before being heated to 110° C. and stirred at 110° C. for 1-2 h (homogeneous solution was observed). When LC/MS indicated the reaction was deemed complete, the reaction mixture was cooled first to room temperature and then in an ice bath to 5° C. The cooled reaction mixture was diluted with a mixture of the saturated aqueous ammonium chloride solution (aq. $NH_4Cl$), the concentrated ammonium hydroxide aqueous solution (aq. $NH_4OH$), and water (4:1:4 by volume, 8.1 L) and the resulting mixture was stirred at room temperature for 30 min. The resulting solids were collected by filtration and dried in a vacuum oven overnight at 45° C. to afford the crude desired product (13). This crude material was then purified by flash chromatography ($SiO_2$, gradient elution with 1% triethylamine in dichloromethane, 2.5% acetone and 1% triethylamine in dichloromethane, 5.0% acetone and 1% triethylamine in dichloromethane, and 10.0% acetone and 1% triethylamine in dichloromethane sequentially) to afford the pure 2-fluoro-4-(7-(quinolin-6-ylmethyl)-imidazo[1,2-b][1,2,4]triazin-2-yl)benzonitrile (13, 127.4 g, 175.4 g theoretical, 72.6% yield) as yellow solids. For 13: $^1H$ NMR (400 MHz, DMSO-$d_6$) δ ppm 9.24 (s, 1H), 8.81 (dd, 1H, J=4.15, 1.66 Hz), 8.26-8.12 (m, 4H), 8.02 (s, 1H), 7.95-7.93 (m, 2H), 7.76 (dd, 1H, J=8.71, 2.08 Hz), 7.47 (dd, 1H, J=8.70, 4.15 Hz), 4.62 (s, 2H); $C_{22}H_{13}FN_6$ (MW 380.38), LCMS (EI) m/e 381.0 ($M^+$+H).

Example 15

6-(3,3-Diethoxyprop-1-ynyl)quinoline (22)

A mixture of 6-bromoquinoline (8, 2.63 g, 12.6 mmol), propargylaldehyde diethyl acetal (3.73 mL, 25.2 mmol, 2.0 equiv), triethylamine (TEA, 12.7 mL, 90.8 mmol, 7.2 equiv), copper(I) iodide (CuI, 24.0 mg, 0.126 mmol, 0.01 equiv), and triphenylphosphine (PPh$_3$, 0.39716 g, 1.5142 mmol, 0.12 equiv) in N,N-dimethylformamide (DMF, 15.6 mL, 202 mmol) was degassed with nitrogen bubbling for 5 min. Palladium acetate (Pd(OAc)$_2$, 0.08499 g, 0.3786 mmol, 0.03 equiv) was added and the mixture was degassed with nitrogen bubbling for 5 min. The reaction mixture was heated to 90° C. under nitrogen with stirring. After 3 h and 10 min, HPLC indicated that the reaction was complete. The reaction mixture was diluted with ethyl acetate (EtOAc, 100 mL) and washed with water (H$_2$O, 2×100 mL). The aqueous layer was extracted with ethyl acetate (EtOAc, 20 mL). The combined organic extracts were then concentrated under the reduced pressure to give the crude product as a black oil. The crude product was purified by flash column chromatography (SiO$_2$, 0-40% EtOAc in hexane gradient elution) to afford 6-(3,3-diethoxyprop-1-ynyl)quinoline (22, 3.2 g, 3.22 g theoretical, 99% yield) as a colorless oil. For 22: $^1$H NMR (400 MHz, DMSO-d$_6$) δ ppm 8.92 (dd, 1H, J=4.35 Hz, 1.86 Hz), 8.36 (d, 1H, J=8.40 Hz, 1.66 Hz), 8.20 (d, 1H, J=1.78 Hz), 7.99 (d, 1H, J=8.71 Hz), 7.76 (dd, 1H, J=8.71 Hz, 1.87 Hz), 7.57 (dd, 1H, J=8.09 Hz, 4.05 Hz), 5.58 (s, 1H), 3.75-3.55 (m, 4H), 1.17 (t, 6H), J=7.16 Hz); C$_{16}$H$_{17}$NO$_2$ (MW 255.31), LCMS (EI) m/e 256.0 (M$^+$+H).

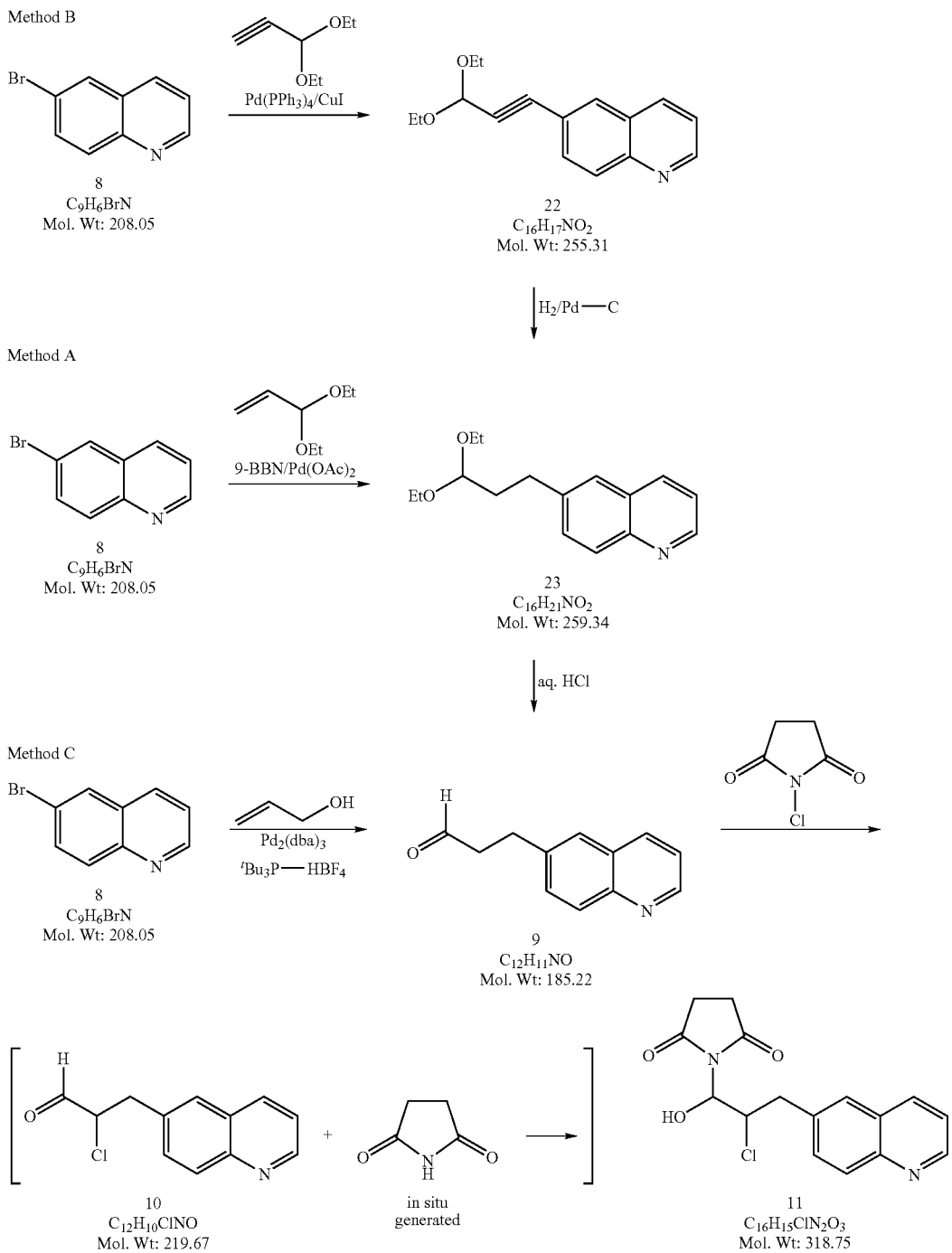

Scheme 2 (Examples 15-18)

Example 16

6-(3,3-Diethoxypropyl)quinoline (23)

Method A. 3,3-Diethoxy-1-propene (548 g, 4.2 mol, 1.75 equiv) was added to a 22 L flask charged with 0.5 M solution of 9-borabicyclo[3.3.1]nonane in tetrahydrofuran (9-BBN solution in THF, 8.4 L, 4.2 mol, 1.75 equiv) at room temperature (the internal temperature raised to 40° C.) over 1 h. The resulting reaction mixture was stirred at room temperature for overnight. At which time $^1$H NMR of an aliquot of the reaction mixture indicated that all the 3,3-diethoxy-1-propene had been consumed. 6-Bromoquinoline (8, 500 g, 2.4 mol, 1.0 equiv), potassium carbonate ($K_2CO_3$, 662 g, 4.8 mol, 2.0 equiv), tricyclohexylphosphine (67.4 g, 0.24 mol, 0.1 equiv), palladium acetate (Pd(OAc)$_2$, 27 g, 0.12 mol, 0.05 equiv) and water (90 mL) were added to the reaction mixture in that order followed by degassing with nitrogen for 0.5 h. The reaction mixture was then heated to reflux for 4 h. Once TLC and LC/MS showed that the starting material had been consumed, the reaction mixture was cooled to room temperature with stirring before being quenched with water (7.5 L) and ethyl acetate (EtOAc, 7.5 L). The layers were separated and the aqueous layer was extracted with ethyl acetate (EtOAc, 4 L). The combined organic layers were washed with a saturated brine solution (NaCl, 4 L), dried over magnesium sulfate (MgSO$_4$) and concentrated under the reduced pressure. The residue was purified by column chromatography (SiO$_2$, 10-60% of ethyl acetate in heptane gradient elution) to afford 6-(3,3-diethoxypropyl)quinoline (23, 520 g, 622.4 g theoretical, 83.5% yield) as a colorless oil. For 23: $^1$HNMR (DMSO-d$_6$, 300 MHz) δ ppm 8.81 (dd, 1H, J=4.23 Hz, 1.73 Hz), 8.28 (d, 1H, J=8.07 Hz), 7.91 (d, 1H, J=8.62 Hz), 7.75 (s, 1H), 7.61 (dd, 1H, J=8.63 Hz, 1.92 Hz), 7.46 (dd, 1H, J=8.25 Hz, 4.22 Hz), 4.46 (t, 1H, J=5.60 Hz), 3.61-3.38 (m, 4H), 2.79 (t, 2H, J=8.53 Hz), 1.95-1.85 (m, 2H), 1.11 (t, 6H, J=6.84 Hz); $C_{16}H_{21}NO_2$ (MW 259.34), LCMS (EI) m/e 260.2 (M$^+$+H).

Method A—Alternative. 9-BBN was generated in situ and used to prepare compound 23 as described as follows: under a nitrogen atmosphere anhydrous 1,2-dimethoxyethane (DME, 47.0 mL) was charged into a 500 mL 3-neck flask equipped with a distillation apparatus. Borane-dimethyl sulfide complex (12.1 g, 151 mmol, 2 equiv) was added and the solution temperature increased from 20 to 22° C. To this solution, 1,5-cyclooctadiene (16.3 g, 151 mmol, 2 equiv) was added dropwise over a period of 30 min to maintain a reaction temperature of 50-60° C., during which time a small amount of dimethyl sulfide was collected by the distillation apparatus. The reaction mixture was then distilled under nitrogen until the distillate temperature reach 84° C. The distillates collected had a volume of ~21 mL. The oil bath was removed and anhydrous THF (49 mL) was added. A small sample of the reaction mixture was taken for $^1$H NMR analysis and the result indicated the olefin was consumed. This 9-BBN solution was used directly for the next step.

To the above 9-BBN solution, 3,3-diethoxy-1-propene (19.3 g, 142 mmol, 1.89 equiv) was added dropwise while maintaining the temperature below 30° C. The reaction is slightly exothermic and white precipitate slowly dissolved. The reaction mixture was then stirred at room temperature for 18 h.

To the solution prepared above, 6-bromoquinoline (8, 15.7 g, 75.4 mmol, 1 equiv), tricyclohexylphosphine (1.27 g, 4.52 mmol, 0.06 equiv), potassium carbonate (20.8 g, 151 mmol, 2 equiv), and water (0.421 mL, 23.4 mmol) were added. The mixture was degassed with nitrogen bubbling for 10-15 min. Palladium acetate (Pd(OAc)$_2$, 0.508 g, 2.26 mmol, 0.03 equiv) was added and the nitrogen bubbling was continued for an additional 10 min. The reaction mixture was heated to 75° C. and maintained at 75-78° C. for 2-3 h. When HPLC showed the completion of the reaction, the heating was discontinued and the reaction mixture was cooled to room temperature. Ethyl acetate (EtOAc, 162 mL) and water (H$_2$O, 162 mL) were added and the organic layer was separated. The aqueous layer was extracted with ethyl acetate (EtOAc, 2×60 mL) and the combined organic extracts were dried over sodium sulfate (Na$_2$SO$_4$) and concentrated under the reduced pressure. The residue was purified by flash column chromatography (silica gel, 0-40% EtOAc in hexane gradient elution) to afford 6-(3,3-diethoxypropyl)quinoline (23, 17.6 g, 19.6 g theoretical, 90% yield) as a clear oil, which was found to be identical to the material made from Method A in every comparable aspect.

Method B. A mixture of 6-(3,3-diethoxyprop-1-yn-1-yl) quinoline (22, 56 mg, 0.22 mmol) and 10% palladium on carbon (5 mg) in THF (5 mL) was hydrogenated under H$_2$ at 1 atm for 6 h. The reaction mixture was filtered through a celite bed and the celite bed was washed with THF (2×2 mL). The combined filtrates were concentrated under the reduced pressure to afford 6-(3,3-diethoxypropyl)quinoline (23, 56 mg, 57 mg theoretical, 98% yield) as a clear oil, which was found to be sufficiently pure to be used in the subsequent reaction without further purification and was identical to the material made from Method A in every comparable aspect.

Example 17

3-(Quinolin-6-yl)propanal (9)

Method 1. A 22 L flask was charged with tris(dibenzylideneacetone)dipalladium(0) (70.0 g, 0.076 mol, 0.015 equiv), tri-tert-butylphosphonium tetrafluoroborate (44 g, 0.152 mol, 0.03 equiv), and dioxane (12 L) at room temperature. The resulting solution was then degassed with a steady stream of nitrogen for 20 min before 6-bromoquinoline (8, 1055 g, 5.07 mol, 1.0 equiv), allyl alcohol (588 g, 10.1 mol, 2.0 equiv), and N-methyl-N-cyclohexylcyclohexylamine (1186 g, 6.08 mol, 1.2 equiv) were added at room temperature. The resulting reaction mixture was stirred at 50- to 55° C. for 8-12 h. When TLC and LC/MS showed that the reaction was deemed complete, the reaction mixture was cooled to room temperature before methyl tert-butyl ether (MTBE, 10 L) was added to the reaction mixture. The resulting mixture was stirred at room temperature for 10 min before being filtered through a plug of celite. The filtrate was concentrated under the reduced pressure and the residue was purified by flash column chromatography (SiO$_2$, 20-80% ethyl acetate in heptane gradient elution) to afford 3-(quinolin-6-yl)propanal (9, 495 g, 939.1 g theoretical, 52.7%) as a yellow oil, which solidified partially upon standing at 0-5° C. For 9: $^1$H NMR (400 MHz, DMSO-d$_6$) δ ppm 9.75 (t, 1H, J=1.24 Hz), 8.83 (dd, 1H, J=4.15 Hz, 1.66 Hz), 8.25 (dd, 1H, J=8.3, 1.03 Hz), 7.93 (d, 1H, J=8.71 Hz), 7.76 (d, 1H, J=1.45 Hz), 7.64 (dd, 1H, J=8.72 Hz, 2.08 Hz), 7.48 (dd, 1H, J=8.30 Hz, 4.36 Hz), 3.05 (t, 2H, J=7.26 Hz), 2.89 (t, 2H, J=7.26 Hz); $C_{12}H_{11}NO$ (MW 185.22), LCMS (EI) m/e 186 (M$^+$+H).

Method 2. A solution of 6-(3,3-diethoxypropyl)quinoline (23, Method A of Example 16, 520 g, 2.08 mol, 1.0 equiv) in ethyl acetate (EtOAc, 2.2 L) was cooled to 0° C. before a 2 N aqueous hydrochloric acid (HCl) solution (2.2 L) was added over 1 h while keeping the reaction temperature below 5° C. The resulting reaction mixture was stirred for an additional 2 h at 0-5° C. When TLC and HPLC/MS indicated the reaction was complete, the reaction was quenched with an ice cold 3 N aqueous sodium hydroxide (NaOH) solution at 0° C. until the pH was between 8 to 9. The layers were separated and the aqueous layer was extracted with ethyl acetate (EtOAc, 2 L). The combined organic layers were washed with brine (2 L), dried with sodium sulfate ($Na_2SO_4$), and concentrated under the reduced pressure to afford crude 3-(quinolin-6-yl)propanal (9, 385.3 g, 385.3 g theoretical, 100%) as a yellow oil, which was found to be identical to the material obtained from Method 1 in every comparable aspect. Since this crude material was found to be sufficiently pure, it was used directly in subsequent reaction without further purification.

Method 3. A 22 L flask charged with 0.5 M solution of 9-borabicyclo[3.3.1]nonane in tetrahydrofuran (9-BBN, 5.75 L, 2.89 mol, 2.0 equiv) and tetrahydrofuran (THF, 6 L) was treated with 3,3-diethoxy-1-propene (393 g, 3.02 mol, 2.10 equiv) at 0-5° C. and the resulting reaction mixture was subsequently warmed to room temperature and stirred at room temperature for 14 h. 6-Bromoquinoline (8, 300 g, 1.44 mol, 1.0 equiv), palladium acetate ($Pd(OAc)_2$, 16.1 g, 0.072 mol, 0.05 equiv), potassium carbonate ($K_2CO_3$, 398 g, 2.89 mol, 2.0 equiv), tricyclohexylphosphine (22.3 g, 0.079 mol, 0.055 equiv), and water (52 g, 2.8 mol) were added to the reaction mixture at room temperature before being degassed with nitrogen for 1 h. The resulting reaction mixture was heated to 75° C. for 1 h. When TLC and LC/MS showed the reaction was deemed complete, the reaction mixture was cooled to room temperature and water (2 L) was added to dissolve the salts. The resulting mixture was then concentrated under the reduced pressure to a volume of approximately 4 L before being filtered through a plug of Celite. The Celite plug was washed with ethyl acetate (EtOAc, 2 L). The filtrate was concentrated under the reduced pressure to a volume of approximately 2 L and this residual solution was then added slowly over 5 min to a flask containing a 2.0 M aqueous hydrochloric acid (HCl) solution (2 L) at 0-5° C. The resulting solution was stirred at 0-5° C. for 14 h before being quenched with saturated aqueous sodium bicarbonate ($NaHCO_3$) solution at 0° C. until the pH was between 8 to 9. The layers were separated and the aqueous layer was extracted with ethyl acetate (EtOAc, 2 L). The combined organic layers were washed with brine (1 L), dried with sodium sulfate ($Na_2SO_4$), and concentrated under the reduced pressure. The residue, which contains the crude 3-(quinolin-6-yl)propanal (9) was purified by flash column chromatography ($SiO_2$, 20-80% ethyl acetate in heptane gradient elution) to afford 3-(quinolin-6-yl)propanal (9, 139 g, 266.7 g theoretical, 52.1%) as a yellow oil, which was found to be identical to the material obtained from Methods 1 and 2.

Example 18

1-(2-Chloro-1-hydroxy-3-(quinolin-6-yl)propyl)pyrrolidine-2,5-dione (11)

Method I. A solution of 3-(quinolin-6-yl)propanal (9, 407 g, 2.2 mol, 1.0 equiv) in chloroform ($CHCl_3$, 1700 mL) was cooled to 0° C. before proline (52 g, 0.44 mol, 0.2 equiv) and N-chlorosuccinimide (NCS, 303 g, 2.31 mol, 1.05 equiv) were added. The resulting reaction mixture was allowed to slowly warm to room temperature (becomes homogeneous) and stirred at room temperature for overnight. The reaction was exothermal to around 40° C. when it reaches room temperature and a precipitate had formed at this point. Once TLC and LC/MS showed that the reaction was deemed complete, the reaction mixture was diluted with ethyl acetate (EtOAc, 1700 mL) and the resulting mixture was cooled to 0° C. The solid was collected by filtration and the collected wet solid cake was placed in a flask and triturated with water (750 mL). The resulting suspension was stirred at room temperature for 30 min before the solids were collected by filtration. The collected solids were washed with water (250 mL) and methyl tert-butyl ether (MTBE, 500 mL) and dried in a vacuum oven at 45° C. to constant weight to afford 1-(2-chloro-1-hydroxy-3-(quinolin-6-yl)propyl)pyrrolidine-2,5-dione (11, 378.7 g, 701.3 g theoretical, 54% yield) as off-white powder. For 11: $^1$HNMR (DMSO-$d_6$, 400 MHz) δ ppm 8.86 (dd, 1H, J=4.15 Hz, 1.66 Hz), 8.33 (dd, 1H, J=8.51 Hz, 1.04 Hz), 7.98 (d, 1H, J=8.72 Hz), 7.85 (d, 1H, J=1.66 Hz), 7.68 (dd, 1H, J=8.51 Hz, 1.87 Hz), 7.51 (dd, 1H, J=8.29 Hz, 4.15 Hz), 7.36 (d, 1H, J=7.05 Hz), 5.28 (dd, 1H, J=9.54 Hz, 6.85 Hz), 5.07 (dt, 1H, J=9.75 Hz, 2.70 Hz), 3.65 (dd, 1H, J=14.52 Hz, 2.49 Hz), 3.09 (dd, 1H, J=14.52 Hz, 9.75 Hz), 2.64 (s, 4H); $C_{16}H_{15}ClN_2O_3$ (MW 318.75), LCMS (EI) m/e 319.2 ($M^+$+H).

Method II. A solution of 3-quinolin-6-ylpropanal (9, 74.8 g, 0.404 mol) in acetonitrile (202 mL, 3.87 mol) was cooled to 0° C. before L-proline (4.70 g, 0.0404 mol, 0.10 equiv), benzoic acid (4.96 g, 0.0404 mol, 0.10 equiv), and N-chlorosuccinimide (NCS, 57.8 g, 0.424 mol, 1.05 equiv) were added at 0° C. The reaction mixture was stirred at 0° C. for 3 h and the resulting clear solution was allowed to warm to room temperature and stirred at room temperature for 18 h. The reaction mixture became a thick suspension and LCMS showed the completion of the reaction. Ethyl acetate (EtOAc, 202 mL) was added to the reaction mixture and the resulting mixture was stirred at room temperature for 1 h. The solids were collected by filtration, washed with ethyl acetate (EtOAc, 100 mL) and dried under vacuum at 40-45° C. to constant weight to afford 1-(2-chloro-1-hydroxy-3-(quinolin-6-yl)propyl)pyrrolidine-2,5-dione (11, 88.8 g, 128.8 g theoretical, 69% yield) as an off-white powder, which was found to be identical to the material made from method I in every comparable aspect.

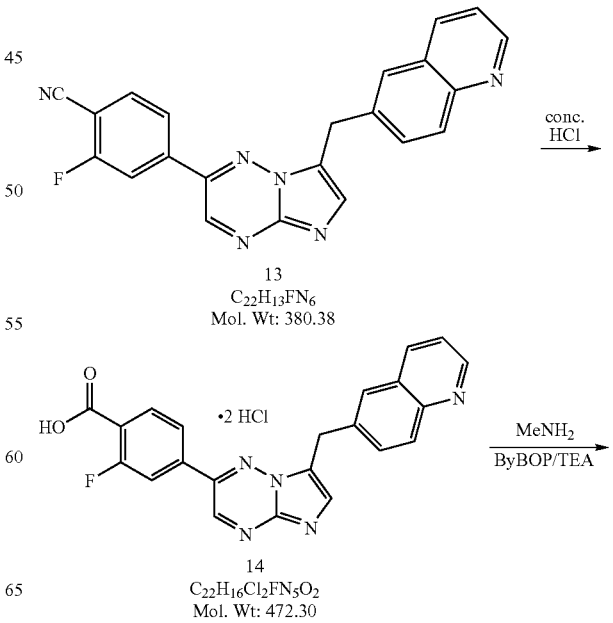

Scheme 3 (Examples 19-21)

-continued

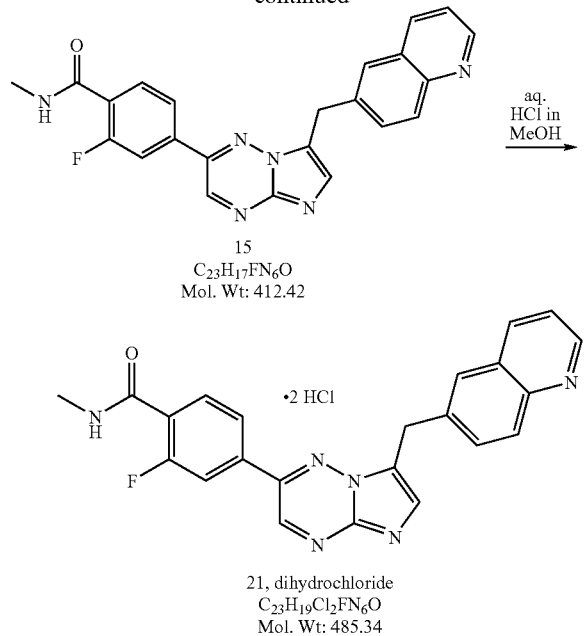

15
C₂₃H₁₇FN₆O
Mol. Wt: 412.42 aq. HCl in MeOH 21, dihydrochloride
C₂₃H₁₉Cl₂FN₆O
Mol. Wt: 485.34

Example 19

2-Fluoro-4-(7-(quinolin-6-ylmethyl)imidazo[1,2-b][1,2,4]triazin-2-yl)benzoic acid (14)

A suspension of 2-fluoro-4-(7-(quinolin-6-ylmethyl)imidazo[1,2-b][1,2,4]triazin-2-yl)benzonitrile (13, 277.5 g, 0.73 mol, 1.0 equiv) in concentrated hydrochloric acid (2500 mL) and water (250 mL) was heated to 100° C. (homogenous at this point) and stirred at around 100° C. for 18 h. When LC/MS indicated the reaction was deemed complete, the reaction mixture was cooled down to 70-80° C. before being diluted with water (2500 mL). The resulting diluted reaction mixture was then cooled down to room temperature (yellow solid forms at 40-50° C.) and subsequent to 0-5° C. The solids were then collected by filtration, washed with a small amount of 1N aqueous HCl (100 mL), and dried in a vacuum oven at 45° C. to constant weight to afford 2-fluoro-4-(7-(quinolin-6-ylmethyl)imidazo[1,2-b][1,2,4]triazin-2-yl)benzoic acid (14, 271 g, 291.5 g theoretical, 93% yield) as yellow to bright-yellow powders. For 14: $^1$H NMR (400 MHz, DMSO-d$_6$) δ ppm 9.34 (s, 1H), 9.23 (dd, 1H, J=5.19 Hz, 1.45 Hz), 9.08 (d, 1H, J=8.29 Hz), 8.38 (d, 1H, J=8.92 Hz), 8.30 (d, 1H, J=1.24 Hz), 8.18 (dd, 1H, J=8.72 Hz, 1.87 Hz), 8.12 (s, 1H), 8.08-8.00 (m, 4H), 4.75 (s, 2H); C₂₂H₁₆Cl₂FN₅O₂ (MW 472.30), C₂₂H₁₄FN₅O₂ (free base: MW 399.38), LCMS (EI) m/e 400.0 (M⁺+H).

Example 20

2-Fluoro-N-methyl-4-(7-(quinolin-6-ylmethyl)imidazo[1,2-b][1,2,4]triazin-2-yl)benzamide (15)

A suspension of 2-fluoro-4-(7-(quinolin-6-ylmethyl)imidazo[1,2-b][1,2,4]triazin-2-yl)benzoic acid (14, 431.4 g, 0.914 mol, 1.0 equiv) and (benzotriazol-1-yloxy)tripyrrolidinophosphonium hexafluorophosphate (PyBOP, 570 g, 1.1 mol, 1.2 equiv) in N,N-dimethylformamide (DMF, 3700 mL) was treated with a solution of 2 M methylamine in THF (1830 mL, 3.656 mol, 4.0 equiv) over 15 min at room temperature. The reaction temperature increased to 30° C. during the addition of methylamine and the reaction mixture became homogeneous once the addition of methylamine was complete. Triethylamine (TEA, 382 mL, 2.742 mol, 3.0 equiv) was then added to the reaction mixture and the resulting reaction mixture was stirred at room temperature for 2-4 h. When LC/MS showed the coupling reaction was deemed complete, the reaction mixture was treated with water (950 mL). The resulting suspension was cooled down to 0-5° C. in an ice-bath and stirred at 0-5° C. for 30 min. The solids were collected by filtration and washed with water (200 mL). The wet solid cake was then suspended in a mixture of water and acetonitrile (1/1 by volume, 2000 mL) and the resulted suspension was stirred at room temperature for 1 h. The solids were collected by filtration, washed with water and acetonitrile, and dried in a vacuum oven at 40-45° C. to constant weight to afford 2-fluoro-N-methyl-4-(7-(quinolin-6-ylmethyl)imidazo[1,2-b][1,2,4]triazin-2-yl)benzamide (15, 322 g, 377 g theoretical, 85.4% yield) as yellow to bright-yellow powders. For 15: $^1$H NMR (400 MHz, DMSO-d$_6$) δ ppm 9.20 (s, 1H), 8.82 (dd, 1H, J=4.05, 1.56 Hz), 8.38 (br m, 1H), 8.27 (dd, 1H, J=8.50 Hz, 1.25 Hz), 8.06-7.93 (m, 5H), 7.81-7.74 (m, 2H), 7.49 (dd, 1H, J=8.40 Hz, 4.35 Hz), 4.62 (s, 2H), 2.78 (d, 3H, J=4.36 Hz); C₂₃H₁₇FN₆O (MW 412.42), LCMS (EI) m/e 413.1 (M⁺+H).

Example 21

2-Fluoro-N-methyl-4-(7-(quinolin-6-ylmethyl)imidazo[1,2-b][1,2,4]triazin-2-yl)benzamide dihydrochloride (21, dihydrochloride)

A suspension of 2-fluoro-N-methyl-4-[7-(quinolin-6-ylmethyl)imidazolo[1,2-b][1,2,4]triazin-2-yl]benzamide (15, 421.2 g, 1.021 mol) in methanol (MeOH, 6600 mL) was heated to 55° C. before a premixed solution of aqueous concentrated hydrochloric acid (conc. HCl, 37 wt. %, 12 M, 420 mL, 5.10 mol, 5.0 equiv) in isopropyl alcohol (IPA, 1510 mL) was added dropwise at 55° C. The resulting clear solution was stirred at 55° C. for 30 min before methyl tert-butyl ether (MTBE, 6750 mL) was added via an additional funnel over 30 min. The solids were slowly precipitated out after addition of methyl tert-butyl ether. The resulting mixture was stirred at 55° C. for an additional 1 h before being gradually cooled down to room temperature. The mixture stirred at room temperature for overnight. The solids were collected by filtration, washed with methyl tert-butyl ether (MTBE, 3×500 mL), and dried in vacuum oven at 45-55° C. to constant weight. The desired 2-fluoro-N-methyl-4-[7-(quinolin-6-ylmethyl)imidazolo[1,2-b][1,2,4]triazin-2-yl]benzamide dihydrochloride (21, dihydrochloride, 470.7 g, 495.5 g theoretical, 95% yield) was obtained as off-white to light yellow crystalline solids. For 21 (dihydrochloride): mp (decom.) 222° C.; $^1$H NMR (400 MHz, DMSO-d$_6$) δ ppm 9.46 (s, 1H), 9.25 (dd, 1H, J=5.4 Hz, 1.4 Hz), 9.12 (d, 1H, J=8.3 Hz), 8.51 (m, 1H), 8.47 (d, 1H, J=0.9 Hz), 8.34 (d, 1H, J=1.3 Hz), 8.23 (s, 1H), 8.21 (dd, 1H, J=9.0 Hz, 1.8 Hz), 8.09-8.02 (m, 3H), 7.79 (dd, 1H, J=7.5 Hz, 8.3 Hz), 4.77 (s, 2H), 2.78 (s, 3H, J=4.5 Hz); $^{13}$C NMR (100 MHz, DMSO-d$_6$) δ ppm 163.4, 159.4 (d, J=249.9 Hz), 145.8, 145.4, 144.5, 143.8, 140.4, 138.8, 136.8, 135.9, 135.7 (J=8.6 Hz), 131.2 (J=3.1 Hz), 130.7, 128.7, 128.2, 126.2 (J=14.9 Hz), 126.0, 123.1 (J=3 Hz), 122.5, 121.0, 114.9 (J=5.6 Hz), 28.4, 26.3; $^{19}$F NMR (376.3 MHz, DMSO-d$_6$) δ ppm −113.2; C₂₃H₁₇FN₆O (free base, MW 412.42), LCMS (EI) m/e 413.1 (M⁺+H) and 435.0 (M⁺+Na).

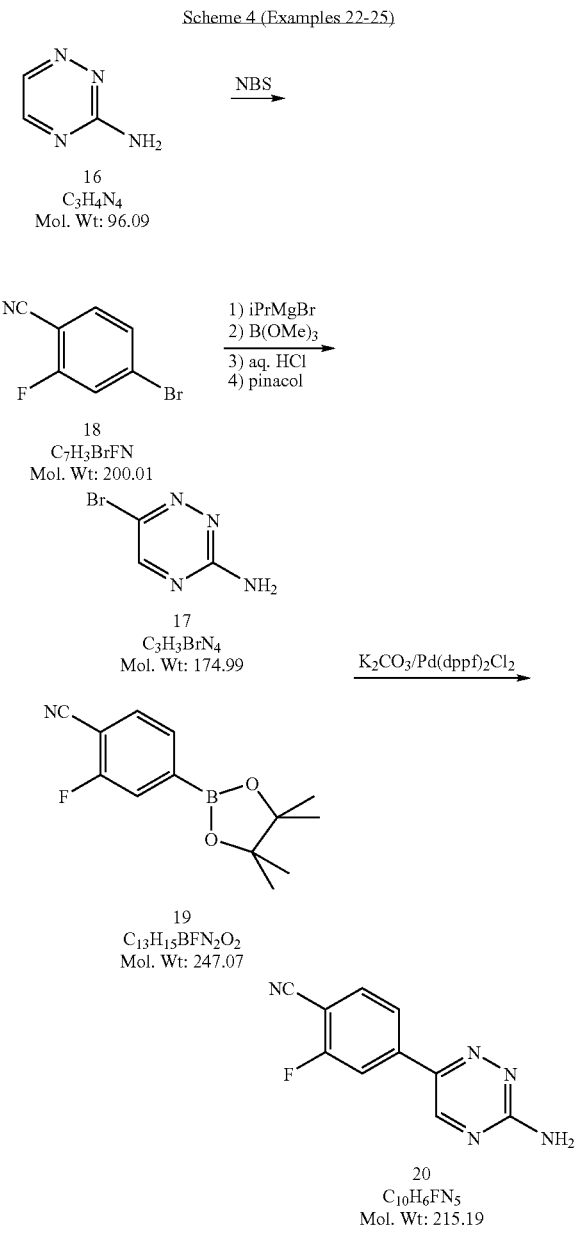

Scheme 4 (Examples 22-25)

Example 22

1,2,4-Triazin-3-amine (16)

An aqueous solution of glyoxal (57 Kg of 40 wt % aqueous solution, 393 mol, 0.73 equiv) was added to a suspension of aminoguanidine bicarbonate (73 Kg, 536.3 mol) in water (400 L) at room temperature. The evolution of carbon dioxide ($CO_2$) began almost immediately. The reaction mixture was then stirred at room temperature for 18 h and the evolution of gas had virtually ceased after about 2 h. The reaction mixture was then filtered, and the filtrate was evaporated to dryness under the reduced pressure. The residue was then extracted with cold methanol (MeOH, 3×120 L), and the combined methanol solution was cooled down to 0-5° C. before being filtered to remove the residual solids. The filtrate was then concentrated under the reduced pressure, and the residue was recrystallized in acetonitrile to afford 1,2,4-triazin-3-amine (16, 34 Kg, 37.76 Kg theoretical, 90% yield) as fine, white needles. For 16: $^1$H NMR (400 MHz, DMSO-$d_6$) δ ppm 8.54 (d, 1H, J=2.33 Hz), 8.20 (d, 1H, J=2.33 Hz), 7.15 (br s, 2H).

Example 23

6-Bromo-1,2,4-triazin-3-amine (17)

A solution of 1,2,4-triazin-3-amine (16, 33 Kg, 343.4 mol) in water (500 L) and acetonitrile (300 L) was treated with N-bromosuccinimide (NBS, 66 Kg, 370 mol, 1.08 equiv) at 5-15° C., and the resulting reaction mixture was stirred at 10-15° C. for 1-4 h. When TLC and LC/MS showed that the bromination reaction was deemed complete, the reaction mixture was treated with an aqueous solution of saturated sodium carbonate ($Na_2CO_3$). The resulting solution was then extracted with ethyl acetate (EtOAc, 3×500 L). The combined organic extracts were washed with water (2×100 L), dried over magnesium sulfate ($MgSO_4$), and concentrated under the reduced pressure to afford 6-bromo-1,2,4-triazin-3-amine (17, 10.3 Kg, 60 Kg theoretical, 17.2% yield) as yellow to brown powders. For 17: $^1$H NMR (400 MHz, DMSO-$d_6$) δ ppm 8.39 (s, 1H), 7.47 (br, 2H); $C_3H_3BrN_4$ (MW 174.99), LCMS (EI) m/e 175.0/176.9 ($M^+$+H).

Example 24

2-Fluoro-4-(4,4,5,5-tetramethyl-1,3,2-dioxaborolan-2-yl)benzonitrile (19)

Step 1. A solution of 2-fluoro-4-bromobenzonitrile (18, 12.5 Kg, 62.5 mol) in anhydrous tetrahydrofuran (THF, 30 L) was treated with a solution of isopropylmagnesium chloride generated from magnesium (Mg, 1.8 Kg, 150 mol, 1.2 equiv) an 2-chloropropane (7.2 Kg, 92 mol, 1.47 equiv) in THF (20 L) and 2-(2-(dimethylamino)ethoxy)-N,N-dimethylethanamine (11 Kg, 69 mol, 1.1 equiv) at room temperature. The resulting mixture was then stirred at 12-20° C. for an additional 2 h before being treated with trimethylborate (9 Kg, 86.7 mol, 1.4 equiv) at 10-15° C. The reaction mixture was stirred at 7-16° C. for 40 min. When TLC and LC/MS showed that the reaction was deemed complete, the reaction mixture was quenched with 1 N aqueous hydrochloric acid (HCl, 35 Kg) at room temperature. The quenched aqueous reaction mixture was then extracted with ethyl acetate (EtOAc, 4×35 L). The combined organic extracts were washed with water (50 L), dried over magnesium sulfate ($MgSO_4$), and concentrated under the reduced pressure. The residual solids were then recrystallized from acetonitrile (20 L) and hexanes (45 L) to afford the corresponding crude 3-fluoro-4-cyanophenyl boronic acid (5.0 Kg, 48% yield).

Step 2. A suspension of the crude 3-fluoro-4-cyanophenyl boronic acid (9.2 Kg, 55.8 mol) in cyclohexane (150 L) was treated with pinacol (13.2 Kg, 111.6 mol, 2.0 equiv) at room temperature, and the resulting reaction mixture was warmed to 40° C. for 4 h. When TLC and LC/MS showed that the reaction was deemed complete, the reaction mixture was cooled down to room temperature before being washed with water (2×75 L). The organic layer was then dried over magnesium sulfate ($MgSO_4$) and concentrated under the reduced pressure to afford 2-fluoro-4-(4,4,5,5-tetramethyl-1,3,2-dioxaborolan-2-yl)benzonitrile (19, 11.8 Kg, 13.8 Kg theoretical, 85.6% yield) as a light yellow solid. For 19: $^1$H NMR (300 MHz, DMSO-$d_6$) δ ppm 7.92 (t, 1H, J=7.00 Hz), 7.62 (m, 2H), 1.29 (s, 12H).

Example 25

4-(3-Amino-1,2,4-triazin-6-yl)-2-fluorobenzonitrile (20)

A mixture of 6-bromo-1,2,4-triazin-3-amine (17, 100.0 g, 571.47 mmol) and 2-fluoro-4-(4,4,5,5-tetramethyl-1,3,2-dioxaborolan-2-yl)benzonitrile (19, 145.43 g, 588.61 mmol, 1.03 equiv) in 1,4-dioxane (1200 mL) was stirred at room temperature for 10 min before potassium carbonate ($K_2CO_3$, 355.4 g, 2572 mmol) in water (600 mL) was added to give a deep red solution. The mixture was degassed by bubbling with nitrogen for 10 min before 1,1'-bis(diphenyl phosphino) ferrocene dichloropalladium(II) complex with dichloromethane (1:1) ($Pd(dppf)_2Cl_2$, 14.14 g, 17.14 mmol, 0.03 equiv) was added at room temperature. The resulting reaction mixture was degassed by bubbling with nitrogen for 10 min and then heated at 86° C. under nitrogen. After 2 h, HPLC showed that the reaction was deemed complete, and the reaction mixture was cooled to room temperature and then to 0-5° C. with an ice-water bath. 1,4-Dioxane (400 mL) was added to the cooled reaction mixture before a solution of 3.3 M aqueous hydrochloric acid solution (HCl, 1900 mL) was added dropwise with stirring to adjust pH to 0.40-0.93. The mixture was stirred at room temperature for 30 min and filtered. The solid collected was stirred with 1,4-dioxane (260 mL) and then added 1N HCl (400 mL). The mixture was stirred at room temperature for 10 min and filtered. The filtrate was combined with the filtrate obtained earlier and washed with ethyl acetate (EtOAc, 2×2 L). The combined ethyl acetate extracts was extracted with 1 N aqueous hydrochloric acid solution (HCl, 3×200 mL). The combined aqueous solution was then treated with activated charcoal (20 g) and stirred at room temperature for 30 min. The mixture was filtered through a celite bed and the filtrate was cooled to 0-5° C. with an ice-water bath. A solution of 50% of sodium hydroxide in water (NaOH, 240 mL, 4500 mmol) was added dropwise at 5-12° C. to adjust pH to 10.6-11.6. The mixture was stirred at 0-5° C. for 30 min and then filtered. The solids collected were washed with aqueous ammonium hydroxide (1 to 3 of 28% concentrated $NH_4OH$ to water, 1900 mL) and dried under vacuum at 40-45° C. to constant weight to afford 4-(3-amino-1,2,4-triazin-6-yl)-2-fluorobenzonitrile (20, 101.2 g, 122.9 g theoretical, 82.3% yield) as a off-white powder. For 20: $^1H$ NMR (400 MHz, DMSO-$d_6$) δ ppm 8.94 (s, 1H), 8.12 (d, 1H, J=11.41 Hz), 8.08-8.00 (m, 2H), 7.71 (br s, 2H); $C_{10}H_6FN_5$ (MW 215.19), LCMS (EI) m/e 215.9 ($M^+$+H).

Scheme 5 (Example 26)

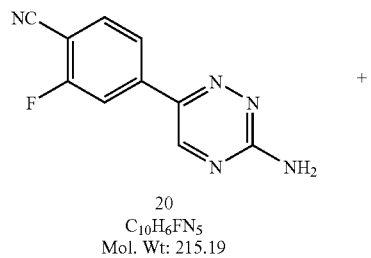

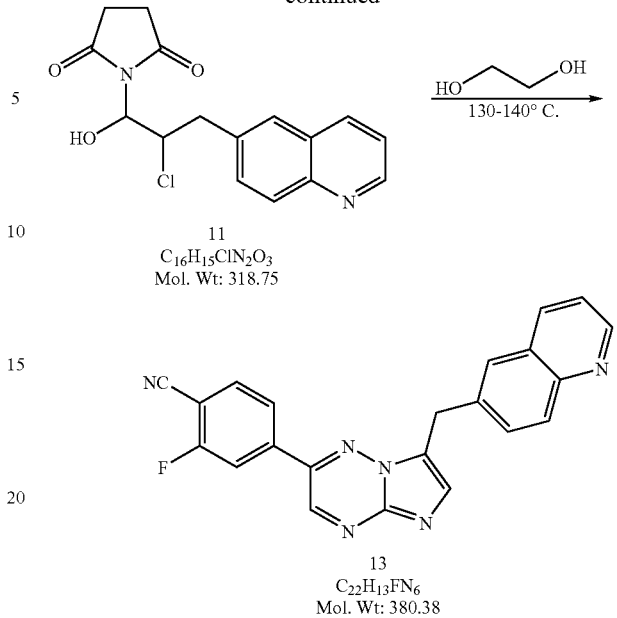

Example 26

2-Fluoro-4-(7-(quinolin-6-ylmethyl)imidazo[1,2-b][1,2,4]triazin-2-yl)benzonitrile (13)

Step 1. A 22 L reactor equipped with a overhead stirring, a thermocouple, a distillation apparatus, and a nitrogen inlet was purged with nitrogen before 4-(3-amino-1,2,4-triazin-6-yl)-2-fluorobenzonitrile (20, 300 g, 1.39 mol), 1-(2-chloro-1-hydroxy-3-(quinolin-6-yl)propyl)pyrrolidine-2,5-dione (11, 635 g, 1.99 mol, 1.43 equiv), and ethylene glycol (3.0 L) were charged to the reactor at room temperature. The resulting reaction mixture was heated to 130-140° C. with nitrogen bubbled through continuously. The distillate was collected with the distillation apparatus. After 3-4 h, HPLC indicated the reaction was deemed complete (presence of <1.5% of starting material 20). The reaction mixture was gradually cooled to room temperature. A 2.5% aqueous sodium carbonate solution ($Na_2CO_3$, 14.1 L) was added with stirring to the reactor over 60 min and the mixture was stirred at room temperature for 1-2 h. The mixture was then filtered, and the solid was washed with water (9.6 L) and dried under vacuum to afford the desired crude product (13, 980.4 g), which was combined with several other batches for purification as described below.

Step 2. A solution of crude product (13, 2754 g) in methylene chloride ($CH_2Cl_2$, 37.8 L) and methanol (0.54 L) was treated with silica gel ($SiO_2$, 2700 g) at room temperature, and the resulting mixture was stirred at room temperature for 90 min. The mixture was filtered and the filter cake was washed with a mixture of $CH_2Cl_2$ (18 L) and methanol (0.26 L). The combined filtrates were treated with silica gel ($SiO_2$, 1800 g) and the resulting mixture was stirred at room temperature for 90 min and then filtered. The filter cake was washed with a mixture of $CH_2Cl_2$ (18 L) and methanol (0.26 L). The combined filtrates were concentrated under the reduced pressure at 20-60° C. to about 8-12 L. The residue was treated with a mixture of isopropanol (IPA) and water (1:1, 9 L) in portions and the distillation was continued at 1 atm pressure until the temperature reached 68-75° C. The mixture was cooled to room temperature and the solids were collected by filtration. The solids collected were washed with isopropanol (IPA, 3.6 L) and dried under vacuum at 40-45° C. to constant weight to afford pure 2-fluoro-4-(7-(quinolin-6-ylmethyl)imidazo[1,2-b][1,2,4]triazin-2-yl)benzonitrile (13, 940.27 g) as a bright yellow powder. The above reaction and purification process gave product 13 in 59-64% yield. The spectroscopic data of compound 13 made by this synthetic process was found to be identical to those obtained from material made by cyanation of compound 12 described previously. For 13: $^1$H NMR (400 MHz, DMSO-$d_6$) δ ppm 9.24 (s, 1H), 8.81 (dd, 1H, J=4.15, 1.66 Hz), 8.26-8.12 (m, 4H), 8.02 (s, 1H), 7.95-7.93 (m, 2H), 7.76 (dd, 1H, J=8.71, 2.08 Hz), 7.47 (dd, 1H, J=8.70, 4.15 Hz), 4.62 (s, 2H); $C_{22}H_{13}FN_6$ (MW 380.38), LCMS (EI) m/e 381.0 (M$^+$+H).

theoretical, 99.8% yield) as a light yellow solid, which was found to be identical to the material made by earlier method. For 14: $^1$H NMR (400 MHz, DMSO-$d_6$) δ ppm 9.34 (s, 1H), 9.23 (dd, 1H, J=5.19 Hz, 1.45 Hz), 9.08 (d, 1H, J=8.29 Hz), 8.38 (d, 1H, J=8.92 Hz), 8.30 (d, 1H, J=1.24 Hz), 8.18 (dd, 1H, J=8.72 Hz, 1.87 Hz), 8.12 (s, 1H), 8.08-8.00 (m, 4H), 4.75 (s, 2H); $C_{22}H_{16}Cl_2FN_5O_2$ (MW 472.30), $C_{22}H_{14}FN_5O_2$ (free base: MW 399.38), LCMS (EI) m/e 400.0 (M$^+$+H).

Example 28

2-Fluoro-N-methyl-4-(7-(quinolin-6-ylmethyl)imidazo[1,2-b][1,2,4]triazin-2-yl)benzamide (15)

Method A. To a stirred solution of 2-fluoro-4-(7-(quinolin-6-ylmethyl)imidazo[1,2-b][1,2,4]triazin-2-yl)benzoic acid

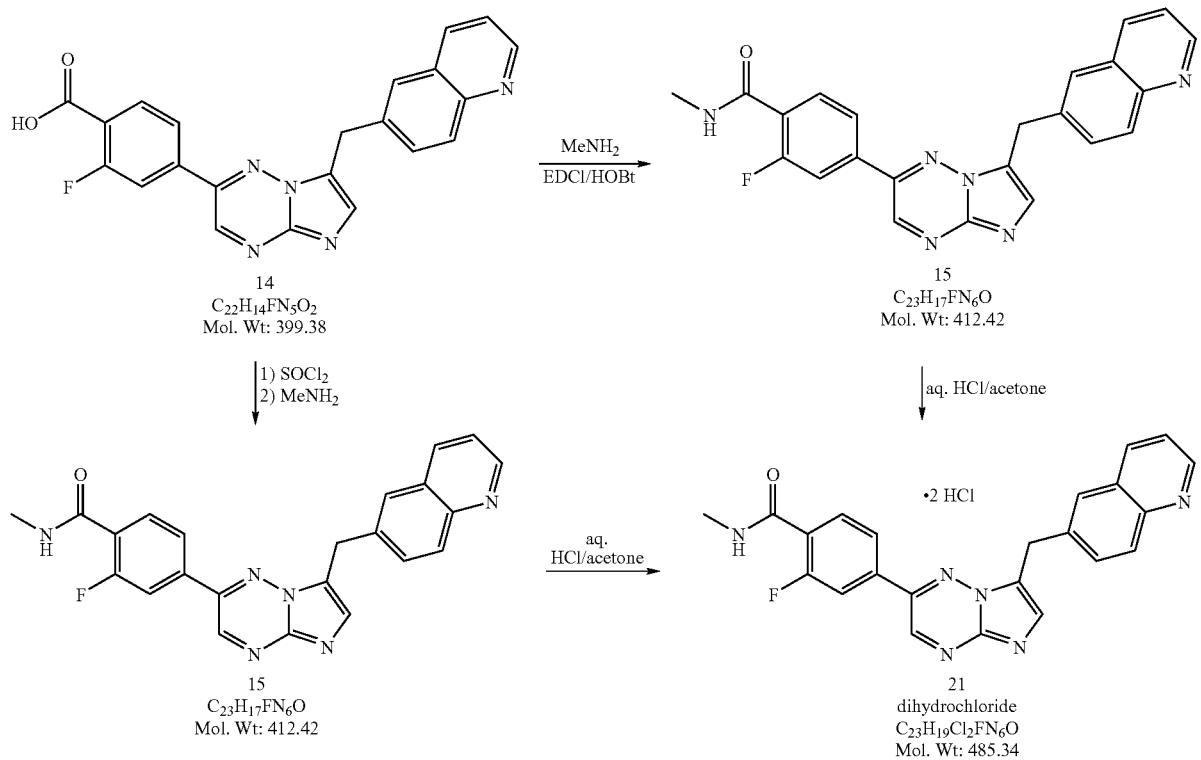

Scheme 6 (Examples 27-29)

Example 27

2-Fluoro-4-(7-(quinolin-6-ylmethyl)imidazo[1,2-b][1,2,4]triazin-2-yl)benzoic acid (14)

To a 22 L reactor equipped with a overhead stirring, a thermocouple, and a nitrogen inlet was charged compound 13 (900 g, 2.37 mol), water (0.9 L), and concentrated HCl (9.1 L) at room temperature. The resulting reaction mixture was heated at 100° C. for 12 h. When HPLC showed the reaction was complete, the reaction mixture was cooled to 90° C. and water (4.9 L) was added over 15 min while maintaining the temperature at 65-90° C. The reaction mixture was further cooled to room temperature and stirred at room temperature for 3 h. The solids were collected by filtration, washed with water (1.2 L) and dried in vacuum at 40-45° C. to constant weight to afford 2-fluoro-4-(7-(quinolin-6-ylmethyl)imidazo [1,2-b][1,2,4]triazin-2-yl)benzoic acid (14, 945 g, 946.5 g (14, 1000 g, 2.12 mol) in acetonitrile (5 L) and $CH_2Cl_2$ (10 L) were charged HOBt (358 g, 2.65 mol, 1.25 equiv), and EDC hydrochloride (508.4 g, 2.65 mol, 1.25 equiv) at room temperature. Another portion of $CH_2Cl_2$ (10 L) was then added to the reaction mixture and the resulting reaction mixture was stirred at room temperature for 20 min. A 2.0 M solution of methylamine (MeNH$_2$) in THF (3.44 L, 6.88 mol, 3.25 equiv) was added with stirring while maintaining the temperature at 15-30° C. The reaction mixture was stirred at room temperature for 2 h before an additional portion of 2.0 M solution of methylamine (MeNH$_2$) in THF (1.06 L, 2.12 mol, 1 equiv) was added. The reaction mixture was stirred at room temperature for 1 h and a second portion of EDC hydrochloride (406 g, 2.12 mol, 1 equiv) was added and the stirring was continued for 6 h. When HPLC showed less than 1% of starting material (14) was remaining, the reaction mixture was concentrated under the reduced pressure at <50° C. During distillation acetonitrile (20 L) was added and distillation was continued until the remaining volume was about 20 L. The residue was treated with an aqueous solution of 2.5% sodium carbonate ($Na_2CO_3$, 40 L) and the resulting mixture was stirred at room temperature for 30 min. The solids were collected by filtration, washed with water (3×4.0 L), air dried by pulling vacuum on the filter to afford the crude desired product (15). The crude solids were treated with $CH_2Cl_2$ (17.6 L) and MeOH (5.2 L) at room temperature and resulting mixture was stirred until a clear solution was obtained. The solution was filtered to remove insoluble materials. With vigorous stirring a 2.5% aqueous solution of sodium carbonate ($Na_2CO_3$, 17.6 L) was added to the filtrate and the mixture was stirred at room temperature for 60 min to give a suspension. Heptane (20 L) was added and the mixture was stirred for an additional 60 min. The mixture was filtered and the solid was washed sequentially with water (3×4.0 L) and heptane (4.0 L), and dried in vacuum to afford 2-fluoro-N-methyl-4-(7-(quinolin-6-ylmethyl)imidazo[1,2-b][1,2,4]triazin-2-yl)benzamide (15, 1095.3 g, 874.3 g theoretical) as a bright yellow solid, which was found to be not totally dry and to contain ~25% residual solvents. This wet solid was used directly for the subsequent dihydrochloride salt (21) formation reaction without further drying. A small sample was dried completely for spectroscopic analyses and the data were consistent with those obtained by earlier method: For 15: $^1$H NMR (400 MHz, DMSO-$d_6$) δ ppm 9.20 (s, 1H), 8.82 (dd, 1H, J=4.05, 1.56 Hz), 8.38 (br m, 1H), 8.27 (dd, 1H, J=8.50 Hz, 1.25 Hz), 8.06-7.93 (m, 5H), 7.81-7.74 (m, 2H), 7.49 (dd, 1H, J=8.40 Hz, 4.35 Hz), 4.62 (s, 2H), 2.78 (d, 3H, J=4.36 Hz); $C_{23}H_{17}FN_6O$ (MW 412.42), LCMS (EI) m/e 413.1 ($M^++H$).

Method B. 2-Fluoro-4-[7-(quinolin-6-ylmethyl)imidazo[1,2-b][1,2,4]triazin-2-yl]benzoic acid dihydrochloride (14, 50.00 g, 0.1059 mol) was added toluene (300 mL) and followed by thionyl chloride ($SOCl_2$, 77.2 mL, 1.06 mol, 10.0 equiv) at room temperature. The resulting reaction mixture was heated at 72° C. under $N_2$ and the reaction was followed by HPLC analysis of the disappearance of the starting material benzoic acid (14). After 48 h, HPLC indicated ~4% starting material remaining and the reaction was stopped. The reaction mixture was concentrated to dryness by vacuum distillation at 40-50° C. The residual solids were added toluene (300 mL) and the solvent was removed by vacuum distillation at 40-50° C. THF (250 mL) was added and the mixture was cooled with an ice-water bath. A 2.0 M of methylamine ($MeNH_2$) in THF (529 mL, 1.06 mol, 10 equiv) was added dropwise. The resulting reaction mixture was allowed to warm up to room temperature and stirred at room temperature for 17 h. Water (600 mL) was added to the reaction mixture and THF (400-500 mL) was removed by vacuum distillation at 40° C. Sodium carbonate (15.60 g, 0.147 mol) was added and the mixture was stirred at room temperature for 30 min. The mixture was filtered and the solid was washed with water (3×30 mL) and dried. The solid was dissolved in pre-mixed methylene chloride ($CH_2Cl_2$, 1000 mL) and methanol (MeOH, 300 mL). With vigorous stirring, a solution of 0.236 M of sodium carbonate ($Na_2CO_3$) in water (1000 mL) was added dropwise. Solid was slowly precipitated out after addition of aqueous solution of sodium carbonate ($Na_2CO_3$). Hexane (1000 mL) was then added dropwise with stirring. The mixture was stirred at room temperature for 30-40 min and the solids were collected by filtration. The solids collected were washed with water (3×200 mL) and dried in vacuum at 40-50° C. to constant weight to afford 2-fluoro-N-methyl-4-(7-(quinolin-6-ylmethyl)imidazo[1,2-b][1,2,4]triazin-2-yl)benzamide (15, 42.2 g, 43.67 g theoretical, 96.6% yield) as a bright yellow solid, which was found to be identical to the material made by Method A in every comparable aspect. For 15: $^1$H NMR (400 MHz, DMSO-$d_6$) δ ppm 9.20 (s, 1H), 8.82 (dd, 1H, J=4.05, 1.56 Hz), 8.38 (br m, 1H), 8.27 (dd, 1H, J=8.50 Hz, 1.25 Hz), 8.06-7.93 (m, 5H), 7.81-7.74 (m, 2H), 7.49 (dd, 1H, J=8.40 Hz, 4.35 Hz), 4.62 (s, 2H), 2.78 (d, 3H, J=4.36 Hz); $C_{23}H_{17}FN_6O$ (MW 412.42), LCMS (EI) m/e 413.1 ($M^++H$).

Example 29

2-Fluoro-N-methyl-4-(7-(quinolin-6-ylmethyl)imidazo[1,2-b][1,2,4]triazin-2-yl)benzamide dihydrochloride (21, dihydrochloride)

2-Fluoro-N-methyl-4-(7-(quinolin-6-ylmethyl)imidazo[1,2-b][1,2,4]triazin-2-yl)benzamide (15, 2100 g, containing ~25% residual solvents) and filtered USP water (7.6 L) were charged into a 50 L reactor at room temperature. With stirring a solution of 6 M aqueous hydrochloric acid (HCl, 3 L) was added with an additional funnel. The resulting reaction mixture was stirred at room temperature for 1.5 h. Acetone (30.5 L) was added to the reactor with stirring during 1 h and the resulting mixture was stirred at room temperature for 2.5 h. The solids were collected by filtration, washed with acetone (2×4.3 L) and dried in vacuum to constant weight to afford 2-fluoro-N-methyl-4-(7-(quinolin-6-ylmethyl)imidazo[1,2-b][1,2,4]triazin-2-yl)benzamide dihydrochloride (21, dihydrochloride, 1629.2 g, 1830.6 g theoretical, 89%) as a pale yellowish crystalline powder, which was found to be identical to the material made by previous method in every comparable aspect. For 21 (dihydrochloride): $^1$H NMR (400 MHz, DMSO-$d_6$) δ ppm 9.46 (s, 1H), 9.25 (dd, 1H, J=5.4 Hz, 1.4 Hz), 9.12 (d, 1H, J=8.3 Hz), 8.51 (m, 1H), 8.47 (d, 1H, J=0.9 Hz), 8.34 (d, 1H, J=1.3 Hz), 8.23 (s, 1H), 8.21 (dd, 1H, J=9.0, 1.8 Hz), 8.09-8.02 (m, 3H), 7.79 (dd, 1H, J=7.5, 8.3 Hz), 4.77 (s, 2H), 2.78 (s, 3H, J=4.5 Hz); $^{13}$C NMR (100 MHz, DMSO-$d_6$) δ ppm 163.4, 159.4 (d, J=249.9 Hz), 145.8, 145.4, 144.5, 143.8, 140.4, 138.8, 136.8, 135.9, 135.7 (J=8.6 Hz), 131.2 (J=3.1 Hz), 130.7, 128.7, 128.2, 126.2 (J=14.9 Hz), 126.0, 123.1 (J=3 Hz), 122.5, 121.0, 114.9 (J=5.6 Hz), 28.4, 26.3; $^{19}$F NMR (376.3 MHz, DMSO-$d_6$) δ ppm −113.2; $C_{23}H_{17}FN_6O$ (free base, MW 412.42), LCMS (EI) m/e 413.1 ($M^++H$) and 435.0 ($M^++Na$).

Example 30

Physical characteristics of the 2-fluoro-N-methyl-4-(7-(quinolin-6-ylmethyl)imidazo[1,2-b][1,2,4]triazin-2-yl)benzamide dihydrochloride salt (21)

The dihydrochloric acid salt is an off-white to light yellow powder as confirmed by visual inspection against a white background.

Example 31

Solubility Study

The solubility of the dihydrochloride (21, See Example 21) at 25° C. was found to be approximately 4.9 mg/mL in water; 0.002 mg/mL in pH 7.4 buffer; 0.002 mg/mL in pH 8.0 buffer; and approximately 24 mg/mL in 0.1 N aqueous HCl. The equilibrium solubility was determined by mixing the sample in the selected aqueous solvents (0.1 N HCl, water, pH 7.4 buffer, and pH 8.0 buffer) for at least 12 hours. The sample concentration was then determined by HPLC using a single point calibration.

Example A

In Vitro c-Met Kinase Enzyme Assays

2-Fluoro-N-methyl-4-[7-(quinolin-6-ylmethyl)imidazolo[1,2-b][1,2,4]triazin-2-yl]benzamide was screened in vitro for its ability to inhibit c-Met kinase activity. The $IC_{50}$ value for the inhibition of c-Met kinase was determined as described in the literature with some modifications (Wang, X. et al, Mol. Cancer Ther. 2003, 2(11):1085-1092; Calic, M. et al., Croatica Chemical ACTA. 2005, 78(3):367-374). Briefly, histidine-tagged c-Met catalytic domain fusion protein (Invitrogen, #PV3143) was used for the assay. $IC_{50}$ measurements were based on the degree of phosphorylation of poly Glu-Tyr (Sigma-Aldrich, #P0275) that was coated (0.01 mg/per well) on 96-well microplates (R&D systems, #DY990). The reaction was carried out in a 50 µL solution containing 50 mM HEPES (pH 7.5), 10 mM $MnCl_2$, 10 mM $MgCl_2$, 0.5 mM DTT, 100 µM $Na_3VO_4$, 5 µM ATP (Cell Signaling Technology, #9804) and serial dilutions of the test compound. The reaction lasted for 25 minutes at 30° C. After the reaction was completed, the contents of the plates were discarded. Plates were then washed with TBS-T (250 µL/well, 5×) and then blocked with TBS-T containing 1% BSA for 2 hours. The contents of the plates was discarded, and 100 µL (per well) of peroxidase-labeled anti-phospho-tyrosine antibody (Sigma, #A5964) diluted (1:60,000) in 1% BSA containing TBS-T were then added and incubated for 1 hour. Plates were washed with TBS-T (250 µL/well, 5×) and followed by the color reaction using 100 µL (1:1 mixture) of $H_2O_2$ and tetramethylbenzidine (R&D Systems, #DY999). The reaction was stopped in minutes with 100 µL of 2 N $H_2SO_4$. The optical density was measured immediately using a microplate reader at 450 nm with wavelength correction at 540 nm. $IC_{50}$ values were calculated with the GraphPad Prism software. The linear range (i.e., the time period over which the rate remained equivalent to the initial rate) was determined for the kinase and $IC_{50}$ determinations were performed within this range.

Wang, X., et al. Potent and selective inhibitors of the Met [hepatocyte growth factor/scatter factor (HGF/SF) receptor] tyrosine kinase block HGF/SF-induced tumor cell growth and invasion. Mol. Cancer Ther. 2003, 2(11):1085-1092.

Calic, M., et al. Flavonoids as inhibitors of Lck and Fyn kinases. Croatica Chemica ACTA. 2005, 78(3):367-374.

2-Fluoro-N-methyl-4-[7-(quinolin-6-ylmethyl)imidazolo[1,2-b][1,2,4]triazin-2-yl]benzamide found to have an $IC_{50}$ value less than 500 nM. See, e.g., U.S. Ser. No. 11/942,130.

Example B

Cell Proliferation/Survival Assays

Cell lines representing various human cancers (SNU-1 and SUN-5 gastric, A549 and NCI-H441 lung, U-87 glioblastoma, HT-29 colon, 786-O kidney, PC-3 pancreatic) can be obtained from American Type Culture Collection and routinely maintained in culture media and conditions recommended by ATCC. Optimal cell density used in proliferation/survival assay can be predetermined for individual cell lines. Compounds are screened for their ability to inhibit cell proliferation/survival, and $IC_{50}$ values are determined. Below are the sample protocols for SNU-5 and SNU-1 cell proliferation/survival assays. SNU-5 and SNU-1 cells are seeded into 96 well cell culture plates at 4000 cells/well and 2000 cells/well respectively in appropriate media containing 2% FBS and supplemented with serial dilutions of individual compounds in a final volume of 100 µL/well. After 72 hour incubation, 24 µL of CellTiter 96® AQueous One Solution reagent (Promega, #G3581) are added to each well (final concentration=333 µg/mL), and the plates are incubated for 2 more hours in a 37° C. incubator. The optical density is measured in the linear range using a microplate reader at 490 nm with wavelength correction at 650 nm. $IC_{50}$ values are calculated with the GraphPad Prism software. For proliferation assays using A549, NCI-H441, U-87, HT-29, 786-0 and PC-3 cells, the cells are first starved for 48 hours in low serum condition (0.1-0.5% FBS in appropriate culture media), then treated with different concentrations of compounds for 2 hours. After the cells are treated with HGF (50 ng/mL) (R&D, #294-HGN) for 24 hours, CellTiter 96® AQueous One Solution reagent is added and plates are incubated for 2 hours. The results are recorded with a plate reader.

Example C

Cell-Based c-Met Phosphorylation Assays

The inhibitory effect of compounds on c-Met phosphorylation in relevant cell lines (SNU-5 gastric, A549 and NCI-H441 lung, U-87 glioblastoma, HT-29 colon, 786-O kidney and PC-3 pancreatic cancer cell lines and HUVEC cell line) can be assessed using immunoblotting analysis and ELISA-based c-Met phosphorylation assays. Cells are grown in appropriate culture media and treated with various concentrations of individual compounds. For SNU-5, HT-29, 786-0 cells, cells are grown in appropriated media supplemented with 0.2% or 2% FBS and treated with compounds for 3-4 hours. Whole cell protein extracts are prepared using reagents and a protocol (#FNN0011) obtained from Biosource International with slight modifications. Briefly, protein extracts are made by incubation in lysis buffer with protease and phosphatase inhibitors [50 mM HEPES (pH 7.5), 100 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 20 minutes. For A549, H441, U-87 and PC-3 cells, cells are serum (0.2% FBS) starved for at least 24 hours, then pretreated with various concentrations of compounds for 1 hour. Whole cell extracts are prepared after the cells were treated with HGF (50 ng/mL) for 10 minutes.

Immunoblotting Analysis

Relevant antibodies are obtained from commercial sources: rabbit polyclonal antibodies included anti-human c-Met (Santa Cruz Biotechnology, #sc-161) and anti-phosphorylated-c-Met (Biosource International, pY1230/4/5 and pY1003). For immunoblotting, 10-20 µg of protein extracts from individual treatment conditions are resolved by electrophoresis on 10% SDS-PAGE gel, and electrotransferred to a nitrocellulose (or PVDF) membrane. The membrane is blocked in PBS containing 3% milk and 0.1% Tween-20 for 1 hour, and then incubated with primary anti-c-Met antibodies in blocking solution for 1 hour. After 3 washes, the membrane is incubated with appropriate horseradish-conjugated secondary antibodies for 1 hour. After final wash, the blot is incubated with chemiluminescence detection reagent for 5 minutes and exposed to X-ray film. The images are scanned, quantified and corrected with total c-Met, and $IC_{50}$ values are calculated. Compounds having an $IC_{50}$ of 10 µM or less are considered active.

ELISA

Cell protein extracts are analyzed using a human phospho-c-Met ELISA kit according to the manufacturer's instructions (R&D Systems, #DYC2480). Optimal amounts of protein extracts are predetermined for individual cell lines. Briefly, for the assay, appropriate amounts of protein extracts are captured with a capture anti-human c-Met antibody for 2 hours in a 96 well microplate. After washes, a detection antibody (HRP-conjugated anti-phospho-tyrosine antibody) is added and incubated for 2 hours. After additional washes, 100 µL of substrate solution (1:1 mixture of $H_2O_2$ and tetramethylbenzidine) are added into each well and the reaction is stopped with 2 N $H_2SO_4$ within an appropriate amount of time during color development. The optical density is measured in the linear range using a microplate reader at 450 nm with wavelength correction at 540 nm. $IC_{50}$ values are calculated with the GraphPad Prism software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt which is 2-fluoro-N-methyl-4-[7-(quinolin-6-ylmethyl)imidazo[1,2-b][1,2,4]triazin-2-yl]benzamide dihydrochloric acid salt, or a hydrate or solvate thereof.

2. A hydrate of the salt of claim 1.

3. The hydrate of claim 2, which is characterized by a melting point of about 220 to about 224° C.

4. The hydrate of claim 2, which is characterized by a melting point of about 222° C.

5. The hydrate of claim 2, which is crystalline.

6. The hydrate of claim 2 having a DSC thermogram which is characterized by an endothermic peak at about 222° C.

7. The hydrate of claim 2, having a DSC thermogram substantially as shown in FIG. 2.

8. The hydrate of claim 2, having a TGA substantially as shown in FIG. 3.

9. The hydrate of claim 2, having an X-ray powder diffraction pattern comprising a characteristic peak expressed in degrees 2θ at about 26.0.

10. The hydrate of claim 2, having an X-ray powder diffraction pattern comprising a characteristic peak expressed in degrees 2θ at about 24.7.

11. The hydrate of claim 2, having an X-ray powder diffraction pattern comprising a characteristic peak expressed in degrees 2θ at about 18.2.

12. The hydrate of claim 2, having an X-ray powder diffraction pattern comprising a characteristic peak expressed in degrees 2θ at about 29.3.

13. The hydrate of claim 2, having an X-ray powder diffraction pattern comprising a characteristic peak expressed in degrees 2θ at about 7.8.

14. The hydrate of claim 2, having an X-ray powder diffraction pattern comprising characteristic peaks expressed in degrees 2θ at about 26.0 and 24.7.

15. The hydrate of claim 2, having an X-ray powder diffraction pattern comprising characteristic peaks expressed in degrees 2θ at about 26.0, 24.7, 18.2, 29.3, and 7.8

16. A composition comprising the salt, or a hydrate or solvate thereof, of claim 1 and at least one pharmaceutically acceptable carrier.

* * * * *